(12) United States Patent
Proulx et al.

(10) Patent No.: US 7,927,316 B2
(45) Date of Patent: Apr. 19, 2011

(54) DISPOSABLE, STERILE FLUID TRANSFER DEVICE

(75) Inventors: Stephen Proulx, Boxboro, MA (US); Joseph Almasian, Westford, MA (US); Naren Renganath, Burlington, MA (US); Stephen Tingley, North Reading, MA (US); Martin Morrissey, Beverly, MA (US)

(73) Assignee: Millipore Corporation, Biilerica, MA (US)

( * ) Notice: Subject to any disclaimer, the term of this patent is extended or adjusted under 35 U.S.C. 154(b) by 0 days.

(21) Appl. No.: 10/500,077

(22) PCT Filed: Apr. 25, 2003

(86) PCT No.: PCT/US03/12927
§ 371 (c)(1),
(2), (4) Date: Jun. 23, 2004

(87) PCT Pub. No.: WO03/090843
PCT Pub. Date: Nov. 6, 2003

(65) Prior Publication Data
US 2005/0016620 A1 Jan. 27, 2005

(51) Int. Cl.
*A61M 5/00* (2006.01)
(52) U.S. Cl. .......................... 604/249; 604/533; 251/319
(58) Field of Classification Search .................. 604/533, 604/249, 537, 256, 905; 251/349, 353, 318, 251/319, 324, 325
See application file for complete search history.

(56) References Cited

U.S. PATENT DOCUMENTS

| | | | |
|---|---|---|---|
| 214,367 | A | 4/1879 | Colvin |
| 988,378 | A | 4/1911 | Olson |
| 1,831,457 | A | 10/1926 | Larsen |
| 1,852,445 | A | 4/1932 | Calkins et al. |
| 2,122,991 | A | 7/1938 | Polston |
| 2,240,888 | A | 5/1941 | Hageline |
| 2,426,808 | A | 12/1943 | Auer |

(Continued)

FOREIGN PATENT DOCUMENTS
DE 8812723 UI 12/1988
(Continued)

OTHER PUBLICATIONS
International Search Report dated Aug. 6, 2003.
(Continued)

*Primary Examiner* — Nicholas D Lucchesi
*Assistant Examiner* — Laura A Bouchelle
(74) *Attorney, Agent, or Firm* — Nields, Lemack & Frame, LLC

(57) ABSTRACT

The present invention relates to a sterile transfer device for fluids, be they liquids or gases. It is comprised of a body having a bore formed through at least a portion of its interior. Preferably, it is a central bore formed through the entire length of the body. Contained within the bore is a movable plunger. The body has a first and a second end. The first end contains a face designed to be attached to the upstream component. The second end is connected to a downstream component such as a filter, pipeline, sample bag and the like. The plunger has corresponding first and second ends. The first end of the plunger when it the closed position is in alignment with the face of the body which combined form a steamable surface and a sterile barrier against the environment to the rest of the interior of the body, the plunger and downstream components.

23 Claims, 24 Drawing Sheets

U.S. PATENT DOCUMENTS

| | | | |
|---|---|---|---|
| 2,642,256 A | 6/1953 | Stehlin | |
| 2,712,881 A | 7/1955 | Mathisen | |
| 2,736,201 A | 2/1956 | Ohlsen et al. | |
| 2,779,350 A | 1/1957 | Owens | |
| 2,844,964 A | 7/1958 | Guibert | |
| 2,859,932 A * | 11/1958 | Mackal | 251/349 |
| 2,865,394 A | 12/1958 | Presley | |
| 3,038,485 A | 7/1961 | Hosek | |
| 3,039,482 A | 6/1962 | Goldberg | |
| 3,097,532 A | 7/1963 | Brown et al. | |
| 3,219,047 A | 11/1965 | Kircher, III et al. | |
| 3,223,100 A | 12/1965 | Koenig et al. | |
| 3,244,376 A | 4/1966 | Thompson | |
| 3,319,622 A | 5/1967 | Shiner | |
| 3,390,677 A | 7/1968 | Razimbaud | |
| 3,424,181 A | 1/1969 | Morse | |
| 3,479,880 A | 11/1969 | Mutter et al. | |
| 3,525,350 A | 8/1970 | Hosek | |
| 3,633,621 A | 1/1972 | Myers | |
| 3,638,499 A | 2/1972 | Saint-Andre | |
| 3,678,959 A | 7/1972 | Liposky | |
| 3,747,411 A | 7/1973 | McDermott et al. | |
| 3,802,782 A | 4/1974 | Natelson | |
| 3,848,851 A | 11/1974 | Cinqualbre et al. | |
| 3,858,449 A | 1/1975 | Singer | |
| 3,921,456 A | 11/1975 | Newcomb, Jr. et al. | |
| 4,064,003 A | 12/1977 | Newton | |
| 4,207,922 A | 6/1980 | Andrieux et al. | |
| 4,294,247 A | 10/1981 | Carter et al. | |
| 4,378,824 A | 4/1983 | Carder, Sr. | |
| 4,423,641 A | 1/1984 | Ottung | |
| 4,423,642 A | 1/1984 | Ottung | |
| 4,454,772 A | 6/1984 | Brunner et al. | |
| 4,458,543 A | 7/1984 | Mieth | |
| 4,479,393 A | 10/1984 | Shores | |
| 4,569,236 A | 2/1986 | Kitchen et al. | |
| 4,580,452 A | 4/1986 | Masson | |
| 4,584,887 A | 4/1986 | Galen | |
| 4,587,856 A | 5/1986 | Otis | |
| 4,587,887 A | 5/1986 | Shibayama et al. | |
| 4,630,847 A | 12/1986 | Blenkush | |
| 4,669,321 A | 6/1987 | Meyer | |
| 4,704,910 A | 11/1987 | Conrad | |
| 4,838,877 A | 6/1989 | Massau | |
| 4,942,901 A | 7/1990 | Vescovini | |
| 4,997,108 A | 3/1991 | Hata | |
| 5,058,619 A | 10/1991 | Zheng | |
| 5,095,765 A | 3/1992 | Filbey et al. | |
| 5,161,417 A | 11/1992 | Strong et al. | |
| 5,177,872 A | 1/1993 | Lewis et al. | |
| 5,246,204 A | 9/1993 | Ottung | |
| 5,296,197 A | 3/1994 | Newbert et al. | |
| 5,360,413 A * | 11/1994 | Leason et al. | 604/249 |
| 5,375,477 A | 12/1994 | Neill et al. | |
| 5,398,557 A | 3/1995 | Shimizu et al. | |
| 5,452,746 A | 9/1995 | Hoobyar et al. | |
| 5,525,301 A | 6/1996 | Newbert et al. | |
| 5,533,983 A | 7/1996 | Haining | |
| 5,542,305 A | 8/1996 | Hollinger | |
| 5,730,418 A | 3/1998 | Feith et al. | |
| 5,747,708 A | 5/1998 | Weiberth | |
| 5,755,155 A | 5/1998 | Buesing | |
| 5,786,209 A | 7/1998 | Newbert et al. | |
| 5,820,614 A * | 10/1998 | Erskine et al. | 604/533 |
| 5,829,425 A | 11/1998 | Woods et al. | |
| 5,911,252 A | 6/1999 | Cassell | |
| 5,948,998 A | 9/1999 | Witte et al. | |
| 6,009,684 A | 1/2000 | Buesing | |
| 6,030,578 A | 2/2000 | McDonald | |
| 6,032,543 A | 3/2000 | Arthun et al. | |
| 6,068,617 A | 5/2000 | Richmond | |
| 6,096,011 A | 8/2000 | Trombley, III et al. | |
| 6,133,022 A | 10/2000 | Newbert et al. | |
| 6,162,206 A * | 12/2000 | Bindokas et al. | 604/533 |
| 6,170,800 B1 | 1/2001 | Meloul et al. | |
| 6,210,372 B1 * | 4/2001 | Tessmann et al. | 604/181 |
| 6,306,191 B1 | 10/2001 | McInerney et al. | |
| 6,314,987 B1 | 11/2001 | Hay | |
| 6,345,640 B1 | 2/2002 | Newbert et al. | |
| 6,354,466 B1 | 3/2002 | Karpisek | |
| 6,386,137 B1 | 5/2002 | Riche | |
| 6,390,127 B2 | 5/2002 | Schick | |
| 6,477,906 B1 | 11/2002 | Peterson | |
| 6,516,677 B1 | 2/2003 | Suter | |
| 6,779,575 B1 | 8/2004 | Arthun | |
| 6,860,162 B1 | 3/2005 | Jaeger | |
| 6,871,669 B2 | 3/2005 | Meyer et al. | |
| 7,293,475 B2 | 11/2007 | Furey et al. | |
| 7,293,477 B2 | 11/2007 | Furey et al. | |
| 7,350,535 B2 | 4/2008 | Liepold et al. | |
| 7,578,205 B2 | 8/2009 | Belongia | |
| 2002/0129858 A1 | 9/2002 | Meyer et al. | |
| 2003/0188588 A1 | 10/2003 | Jaeger | |
| 2005/0132821 A1 | 7/2005 | Furey et al. | |
| 2006/0142730 A1 | 6/2006 | Proulx et al. | |
| 2006/0201263 A1 | 6/2006 | Furey et al. | |
| 2007/0106264 A1 | 5/2007 | Proulx et al. | |
| 2008/0022785 A1 | 1/2008 | Furey et al. | |
| 2009/0019952 A1 | 1/2009 | Furey et al. | |

FOREIGN PATENT DOCUMENTS

| | | |
|---|---|---|
| DE | 100 39 196 | 2/2002 |
| DE | 603 10 700 | 10/2007 |
| EP | 0 107 579 A2 | 5/1984 |
| EP | 01 540 002 B1 | 9/1985 |
| EP | 0 508 749 A2 | 10/1992 |
| EP | 0 468 957 B1 | 6/1994 |
| EP | 0 684 050 | 11/1995 |
| EP | 0684050 | 11/1995 |
| EP | 1008359 A1 | 6/2000 |
| EP | 1 499 382 | 11/2003 |
| EP | 1 548 420 | 6/2005 |
| EP | 1 962 076 A2 | 8/2008 |
| GB | 1573482 | 8/1980 |
| GB | 2327369 | 1/1999 |
| GB | 2365511 | 2/2002 |
| JP | 58-131802 | 9/1983 |
| JP | 2-052667 A | 2/1990 |
| JP | 02-118276 | 5/1990 |
| JP | 02-118276 | 5/1993 |
| JP | 6-023045 A | 2/1994 |
| JP | 06-327772 | 11/1994 |
| JP | 07-051371 | 2/1995 |
| JP | 08-168535 | 7/1996 |
| JP | 9-154945 A | 6/1997 |
| JP | 11-141713 | 5/1999 |
| JP | 11-270705 | 10/1999 |
| JP | 2000-055792 | 2/2000 |
| JP | 2001-170188 A | 6/2001 |
| JP | 2001-269401 A | 10/2001 |
| JP | 4332106 | 7/2005 |
| JP | 2008-185218 | 8/2008 |
| JP | 2009-2965 | 1/2009 |
| JP | 2009-192540 | 8/2009 |
| WO | 9012972 | 11/1990 |
| WO | WO 94/08173 | 4/1994 |
| WO | 9630076 | 10/1996 |
| WO | 9716715 | 5/1997 |
| WO | WO 98 45188 | 10/1998 |
| WO | 9850105 | 11/1998 |
| WO | 9903568 | 1/1999 |
| WO | 99/06089 A1 | 2/1999 |
| WO | 00/78472 A1 | 12/2000 |
| WO | 03090842 | 11/2003 |
| WO | 03090843 A1 | 11/2003 |

OTHER PUBLICATIONS

Notice of Rejection with English Translation, JP 2003-587467, Jul. 24, 2007, 3 pgs.

International Search Report for PCT/US03/12927 dated Aug. 6, 2003.

International Preliminary Examination Report for PCT/US03/12927, dated Feb. 11, 2004.

International Search Report for PCT/US03/13073 dated Aug. 6, 2003.

European Search Report EP 1548420 A3, dated Mar. 13, 2006.

International Search Report for PCT/US03/12924, dated Aug. 6, 2003.
International Preliminary Examination Report for PCT/US03/12924, dated Jul. 8, 2004.
Gore's Preliminary Invalidity Contentions to Plaintiff Millipore Corporation, Document No. 21, filed Oct. 29, 2009 in the United States District Court for the District of Massachusetts, Civil Action No. 09-10765 DPN.
Janetchek, R., "Capsule Filters & Disposable Sterile Processing Systems", Pharmaceutical Processing, p. 8 (Jan. 2001).
Charter Medical, Ltd., Bioprocess Products, "New Quality of Data for Bioprocessings Bags", Pharmaceutical Processing, p. 8 (Jan. 2002).
Greene, R., et al., "Disposable Equipment: A Mainstay in Bioprocessing", Chemical Engineering Progress, pp. 10-11 (Nov. 2002).
Wendt, D., "Disposable processing systems: how suppliers are meeting today's biotech challenges from fluid handling to filtration", Biopharm International, p. 18 (Jul. 2003).
Haughney, H., et al., "Taking Disposable Processing to the Next Level", Biopharm Trends, pp. 20-22 (Jun. 2004).
Tingley, S., "Plastic factory: Disposable biopharmaceutical manufacturing takes a giant leap forward", Alternative Manufacturing, pp. S4-S9 (Feb. 2003).
Tingley, S., "Plastic factory, Part II: The final pieces of the disposable puzzle", Alternative Manufacturing, pp. 12-14 (Jun. 2003).
Aranha, H., et al., "Disposable processing gains you a competitive edge: enhancing manufacturing capacity with disposable filters, connectors, and membrane chromatography", Biopharm International, p. 50 (Oct. 2003).
Millipore's Initial Infringement Contentions, Document No. 19, filed Oct. 8, 2009 in the United States District Court for the District of Massachusetts, Civil Action No. 09-10765 DPW.
Gore's Preliminary Non-Infringement contentions to Plaintiff Millipore Corporation, Document No. 20, filed Oct. 29, 2009 in the United States District Court for the District of Massachusetts, Civil Action No. 09-10765 DPW.
Lynx ST Connectors http://www.millipore.com/catalogue/module/c9131 dated Oct. 30, 2009.
Pure-Flo Hygienic diaphragm valves, actuators, and switch packages, http://www.ittpureflo.com/valvetype.html dated Oct. 30, 2009.
About Fluid Line Technology, http://www//fluidlinetech.com/aboutus.html dated Oct. 30, 2009.
Valves, Gemu Valves and Distributor, Diaphragm Valves, Sanitary Valves, Aseptic Valves, Valves and Fittings, http://www.casellasales.com, dated Oct. 30, 2009.
Allegro Single-use Systems—Recommended Capsule Filters and Membranes, http://www.pall.com/variants/print/biopharm_48022.asp dated Oct. 30, 2009.
Colder Products—Quick Couplings & Fittings for Industrial Applications—Industrial Products, http://www.colder.com/Markets/Industrial/IndustrialProducts/tabid/821/Default.aspx?ProductId=22, dated Oct. 30, 2009.

NovAseptic—How to Use NA sampling system, http://www.novaseptic.se/main.as?typ=6 dated Feb. 13, 2002.
Steam-In-Place Bag Connector, http://www.fluidcomponents.net/tc_tech.html, downloaded on Feb. 18, 2010.
Pharmenta AptiPort Sampling Valve, http://www.web.archive.org/web/20031029084907/http://www.pharmenta.com/aptiport.htm, dated Feb. 18, 2010.
Landon, R., et al., "Process PharmaTEC International", issue Jun. 2004 (RP1007EN00), pp. 16-17 (Nov. 2004).
Daily Business Briefing—"Entegris Introduces the First ALL TEFLON PFA" dated Apr. 16, 2002.
Block, S.S. "Disinfection, Sterilization, and Preservation (Fourth Edition)", Lea & Febiger, ISBN:0-8121-1364-0 (1991).
Opticap Valve; Millipore Application Note, Jul. 2000, Gamma Compatible Sterilizing Grade Filter Capsules for Use with Disposable Manufacturing Container; 6-Pages.
Opticap Vent; Millipore Data Sheet, Apr. 2005, "Gamma Compatible Sterilizing-grade Durapore 0.1 um and 0.22 um Filters"; 8-Pages.
Opticap3; Millipore, Nov. 2001, OpticapTM Capsules with Millistake+TM Media User Guide, 4-Pages.
NovaSeptum, NovAseptic, Feb. 2003, "NovaSeptum Liquid Sampling System", 4-Pages.
Microbiological Analysis, Sampling Ports, 1989, p. 130.
Lnyx Trademark to 2,831,931; Apr. 1, 2003.
Office Action dated Oct. 7, 2010 in corresponding U.S. Appl. No. 11/584,301.
Notice of Allowance and Supplemental Notice of Allowances dated Oct. 1, 2010, Oct. 7, 2010, Oct. 15, 2010 and Oct. 20, 2010 in co-pending U.S. Appl. No. 12/284,666.
Japanese communication dated Jul. 27, 2010 in corresponding foreign application (JP2008-070904).
Office Action dated Mar. 19, 2010 in co-pending U.S. Appl. No. 12/284,666.
Office Actions dated Aug. 19, 2009 and May 12, 2010 in corresponding U.S. Appl. No. 11/350,384.
Office Action dated Mar. 16, 2010 in corresponding U.S. Appl. No. 11/584,301.
Office Actions dated Jan. 30, 2009, Jun. 26, 2009, Aug. 12, 2009, Sep. 25, 2009 and Apr. 6, 2010 in co-pending U.S. Appl. No. 11/878,126.
Memorandum and Order, Document No. 70, dated Sep. 20, 2010, in the United States District Court for the District of Massachusetts, Civil Action No. 09-10765-DPW.
European communication dated Oct. 29, 2010 in a corresponding foreign application (EP10179151.5).
European communication dated Oct. 29, 2010 in a corresponding foreign application (EP10179183.8).
Indian communication dated Oct. 18, 2010 in a corresponding foreign application (IN1444/DELNP/2004).

* cited by examiner

DISPOSABLE, STERILE FLUID TRANSFER DEVICE

The present invention relates to a disposable, sterile fluid transfer device. More particularly, it relates to a disposable sterile fluid transfer device, preferably in the form of a connector or valve for use in the pharmaceutical and biopharmaceutical industry.

BACKGROUND OF THE INVENTION

In the pharmaceutical, biotechnology and even food, beverage and cosmetics industries, it is often desired to provide a processing system that is capable of handling fluids in a sterile manner. This is designed to prevent unwanted, often dangerous organisms, such as bacteria as well as environmental contaminants, such as dust, dirt and the like from entering into the process stream and/or end product. It would be desirable to have a completely sealed system but this is not always possible with the processes that take place in production.

There is a need for the introduction or removal of materials from the process stream in order to add components of the product, such as media or buffers to a bioreactor; withdraw samples from the process stream to check for microbial contamination, quality control, process control, etc; and to fill the product into its final container such as vials, syringes, sealed boxes, bottles and the like.

Typically, the systems have been made of stainless steel and the system is exposed to live steam before use and then cleaned with chemicals such as caustic solutions after use to ensure that all contaminants are removed.

Steaming is the most effective means of sterilization. The use of steam in a set system is known as steaming in place or SIP. Saturated steam carries 200 times the BTU heat transfer capacity of heated air because of the latent heat released by the steam as it changes from vapor to liquid.

Several disadvantages exist with the use of steam. Any connections to or openings of the system made after the system has been SIP'd is an aseptic (but not sterile) connection or opening. This increases the risk of contamination of the entire system. One typically uses alcohol wipes or an open flame to clean the components to be connected, (e.g. connecting a sample collection bag to a system after SIP has occurred) and thus minimize the risk of contamination.

Also the high temperatures and pressure differentials of the steam make the selection of filter materials and components very difficult and limited and even then an accidental pressure differential at high temperatures can cause a filter, membrane or other non-steel component to fail.

Additionally, such systems that are reused need to undergo rigorous testing and validation to prove to the necessary authorities that the system is sterile before each use. The expense of validation as well as the cleaning regiment required is very high and very time consuming (typically taking 1 to 2 years for approval). In addition, some components are very difficult to adequately clean after use in preparation for their next use. Manufacturers are looking for ways to reduce both their costs and the time to market for their products, One possible approach is to adopt an all disposable system that is set up in a sterile fashion, used and then thrown away.

The present invention provides a connector that can be used in either the traditional steel system or disposable system which provides both a means for steam sterilizing the mating point of the connector to the system as well as providing a sterile downstream area or component, in pre-sterile condition, that can be disposed of after use and not be recleaned.

SUMMARY OF THE INVENTION

The present invention relates to a sterile transfer device for fluids, be they liquids or gases. It is comprised of a body having a bore formed through at least a portion of its interior. Preferably, it is a central bore formed through the entire length of the body. Contained within the bore is a movable plunger. The body has a first and a second end. The first end contains a face designed to be attached to the upstream component. The second end is connected to a downstream component such as a filter, pipeline, sample bag and the like. The plunger has corresponding first and second ends. The first end of the plunger when it the closed position is in alignment with the face of the body which combined form a steamable surface and a sterile barrier against the environment to the rest of the interior of the body, the plunger and downstream components.

The downstream components are assembled to the device and it is placed in the closed position. The entire device and downstream components are sterilized, such as with gamma radiation. In use the device and downstream components are attached by the face to the upstream component such as a filter outlet, a tank outlet, a "T" of a pipe and secured in place. The system and the face of the device are then steam sterilized in place. The device is then selectively opened when needed establishing a sterile pathway through the device to the downstream components.

IN THE DRAWINGS

FIGS. 16A-I show other embodiments of the device of the present invention in cross sectional view.

Figure 17:
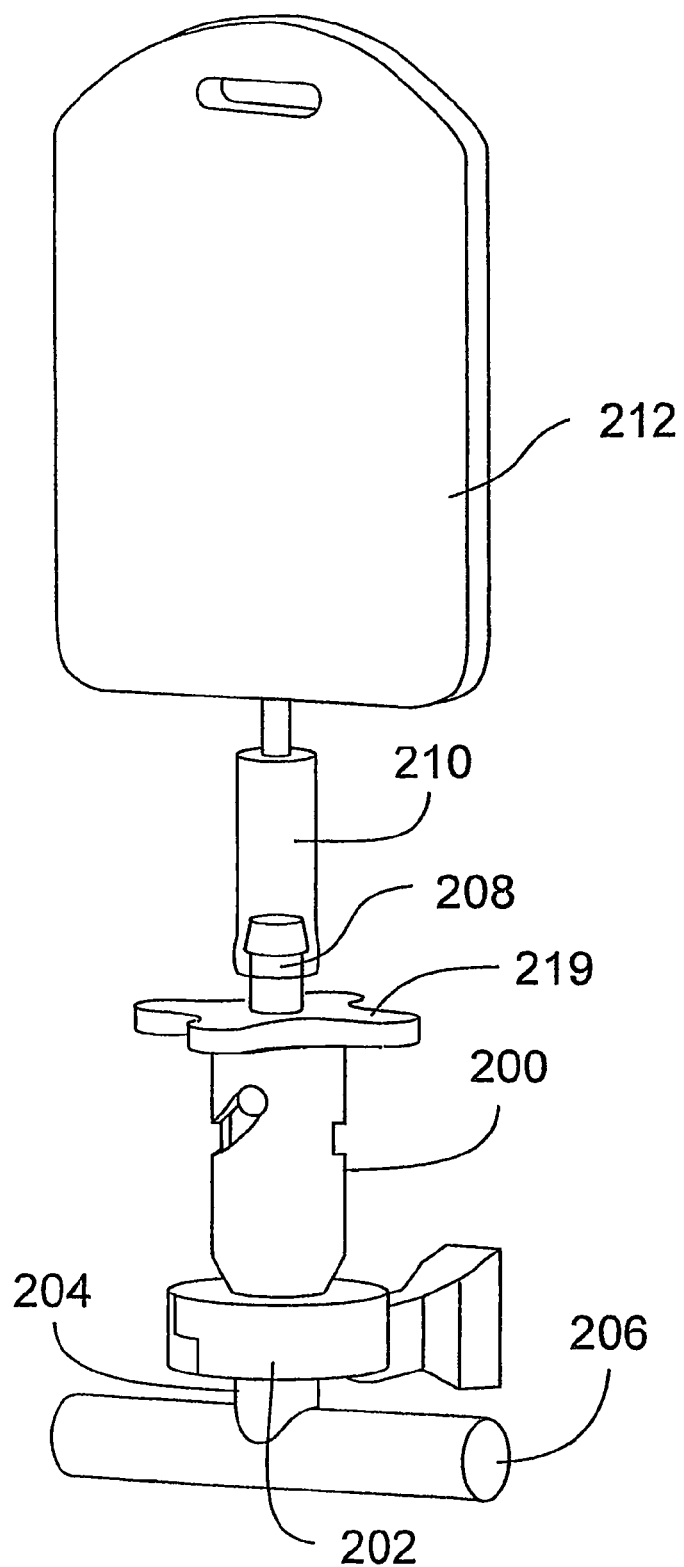

FIG. 17 shows the device of the present invention in one potential application in which there is a sterile to nonsterile connection.

Figure 18:
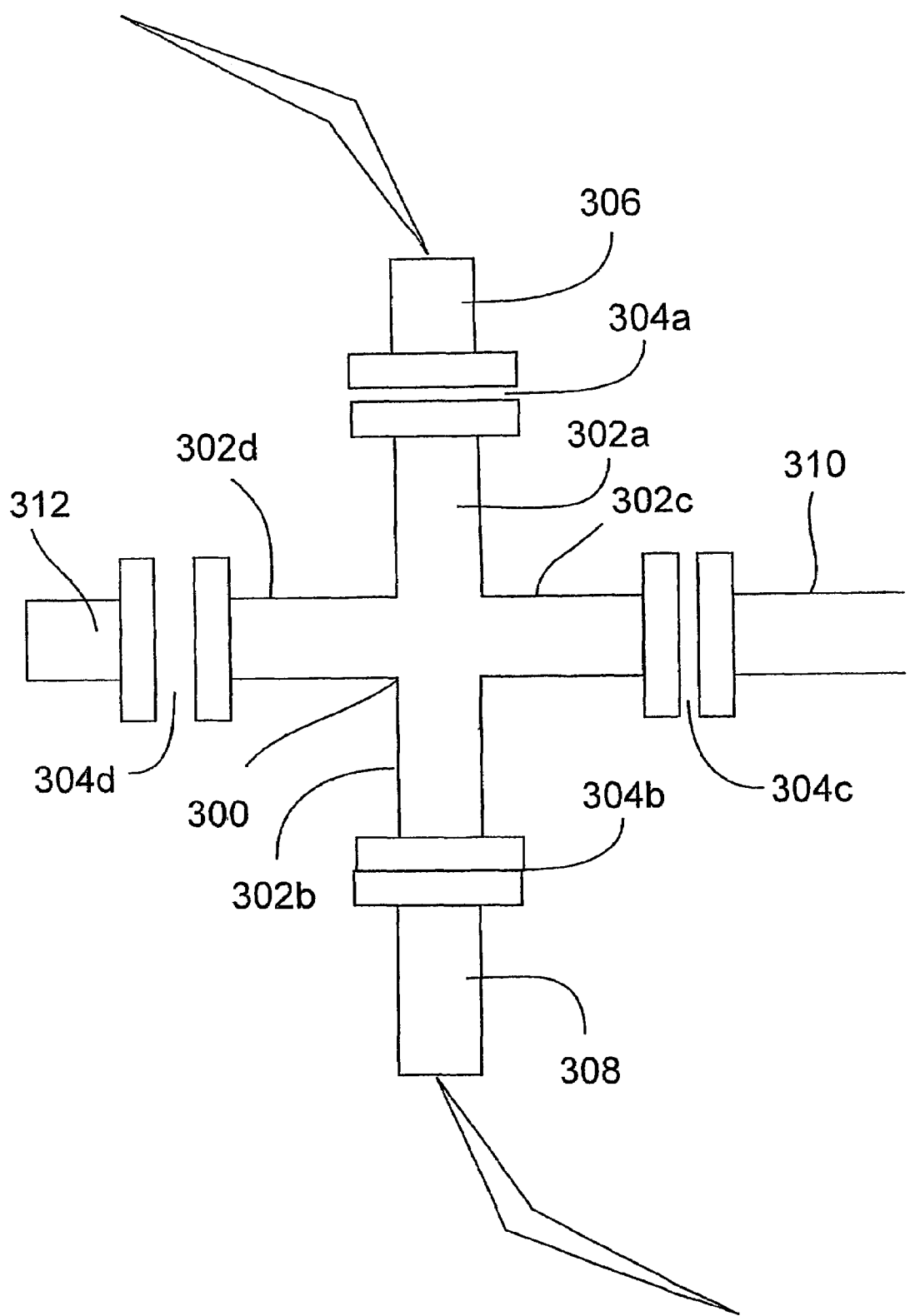

FIG. 18 shows the device of the present invention in one potential application in which there is a sterile to sterile connection.

DETAILED DESCRIPTION OF THE INVENTION

The present invention is a sterile fluid transfer device, preferably in the form of a connector or a valve.

Figure 1:
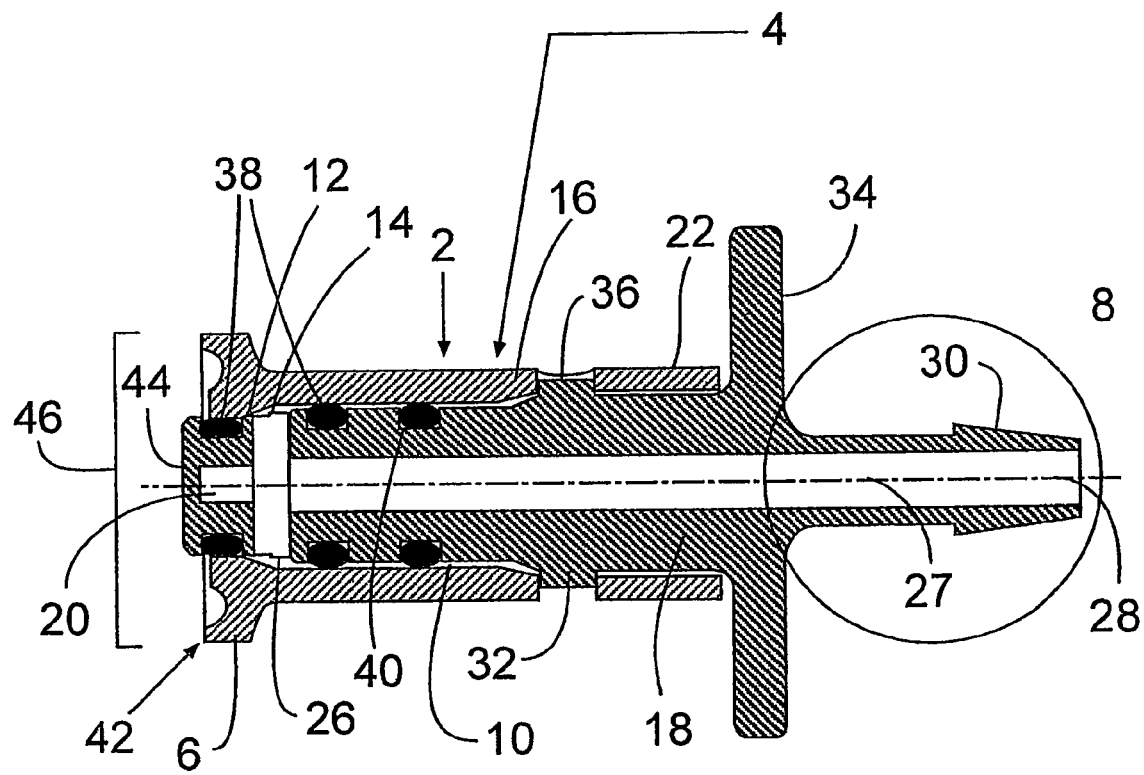
FIG. 1 shows a cross sectional view of a first embodiment of the present invention in a closed position.

A first embodiment of the present invention is shown in FIG. 1. The device 2 is formed of a body 4 having a first end 6 and a second end 8. The body 4 also has a bore 10 extending in this embodiment from the first end 6 to the second end 8. The bore 10 as shown is formed of three sections each with a different diameter. There is the first bore section 12 which has a first set diameter, a transition bore section and a second bore section which has a second set diameter that is greater than the first set diameter of the first bore section 12. The transition bore section 14 is arranged between the first and second bore sections 12, 16 and has an outwardly tapering diameter along its length with the diameter of the transition section 14 adjacent the first bore section 12 being equal to the first set diameter and the diameter of the transition section 14 adjacent the second bore section 16 being equal to the second set diameter. The diameter of the transition section between the first and second bore sections is preferably a linear outward progression between the two bore sections.

Contained within the bore is a plunger 18 which has a shape corresponding to that of the bore 14. The plunger has a first portion 20 having a diameter equal to or less than that of the diameter of the first bore section, a second plunger portion 22 having a diameter equal to or less than that of the second bore section and a transitional portion 24 between the first and the second plunger portions 20, 22 having an outwardly tapered diameter between the first and second plunger portions 20, 22 equal to or less than the diameter of the transition bore section 14. The plunger 18 also contains one or more openings 26 in either the transitional portion 24 or the first or second portions 20, 22 as well as a fluid channel 27 that forms a fluid connection to a downstream component or tubing (not shown).

As shown, the farthest part 28 of the second portion 22 contains a barb design 30 to connect to the next downstream component. The plunger also contains several preferable elements that are useful but not necessary to the invention. Included among these are a cam 32 and a connector handle 34. The cam 32 rides in a cam slot 36 formed in the body 4 and together is used to limit the length of travel of the plunger 18 in the bore 14.

The device is shown in FIG. 1 in the closed position. One or more seals 38 are arranged along the length of the plunger 18 to form a liquid tight seal between various portions of the plunger 18 and the bore 14 when they are in the closed or open positions. As shown the seals 38 are contained in grooves 40.

The device 2 is attached to an upstream component or pipe by a sanitary flange 42 formed as part of the body 4. In the closed position the flange 42 and the farthestmost end of the first portion of the plunger 44 form a face 46 against the rest of the system. The flange 42 can be attached to the upstream component or pipe by a clamp such as a Tri-Clover™ fitting, Ladish™ fitting, ClickClamp™ clamp or the like. This face 46 is capable of withstanding steam treatment when in the device is in the closed position as will be described in more detail below.

Figure 2:
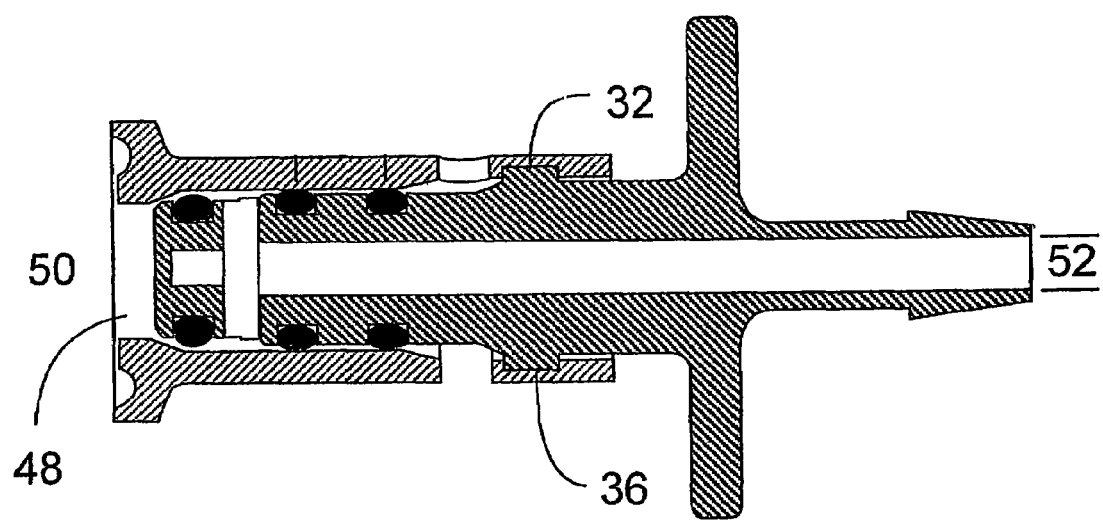
FIG. 2 shows a cross sectional view of the first embodiment of the present invention of FIG. 1 in an open position.

FIG. 2 shows the device 2 of FIG. 1 in the open position. To the extent that the same reference numbers apply to both FIGS. 1 and 2 they have been kept the same.

In FIG. 2, the plunger has been moved from the closed position of FIG. 1 to an open position. The farthestmost end of the first portion of the plunger 44 has been moved back from the face 46 providing a passageway 48 to the bore 14 and the one or more openings 24 and the fluid channel 26 forming a fluid connection between the upstream 50 and downstream sides 52 of the device 2. As shown, the plunger is moved rearward or downstream and rotated at the same time, as evidenced by the movement of the cams 32 in the cam slot 36.

Figure 3:
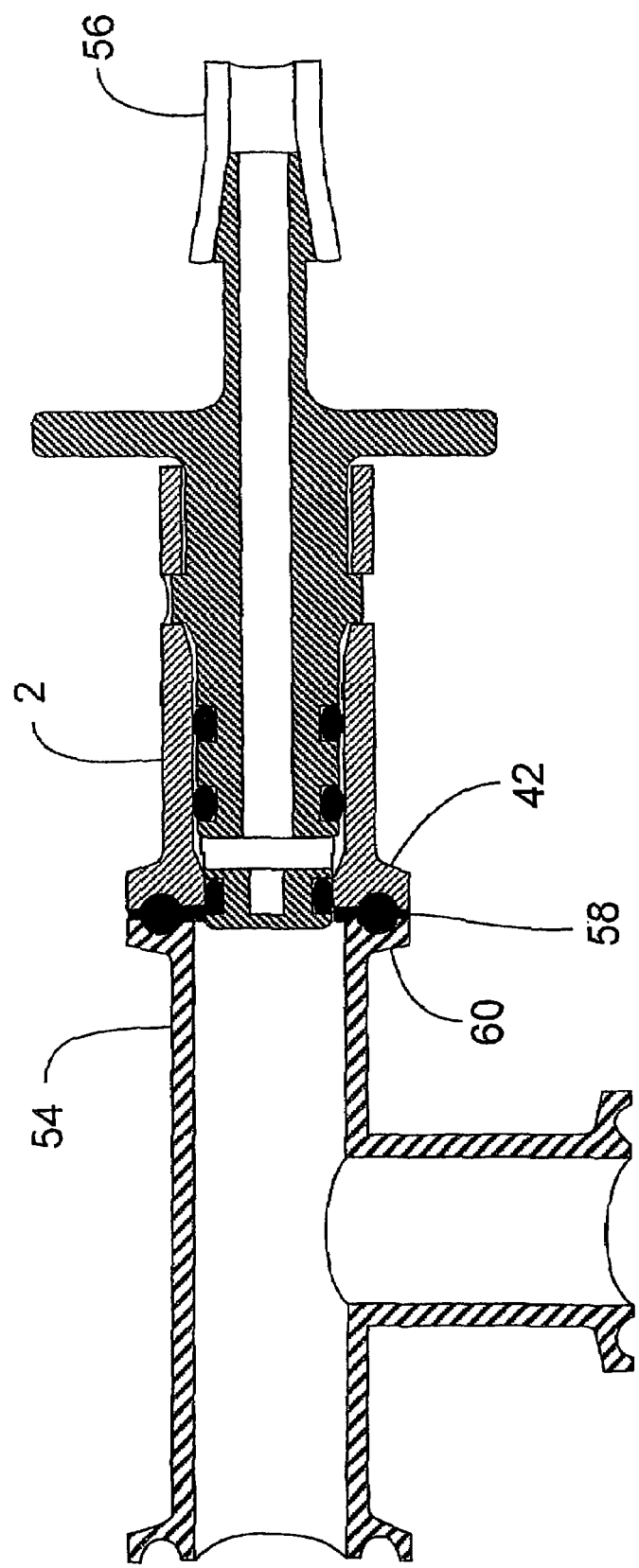
FIG. 3 shows a cross sectional view of the first embodiment of the present invention of FIG. 1 mounted to an upstream component.

FIG. 3 shows the device 2 of FIG. 1 mounted to an upstream component 54, in this instance a "T" pipe and a downstream component 56, in this instance a piece of hose or plastic pipe. Also shown is liquid tight seal 58 formed between the flange of the device 2 and a flange 60 (clamp not shown).

Figure 4:
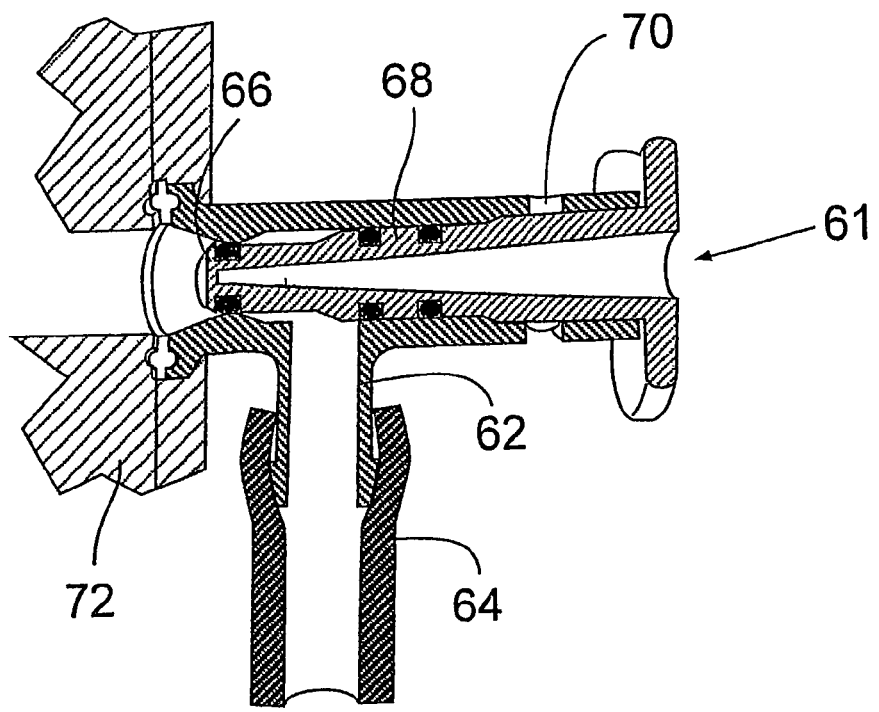
FIG. 4 shows a cross sectional view of a second embodiment of the present invention in a closed position.
Figure 5:
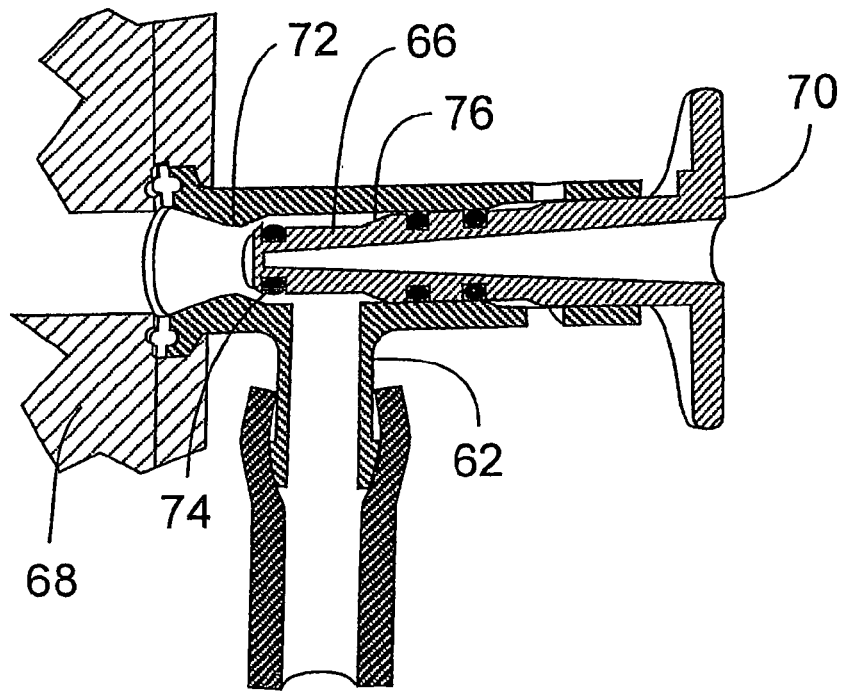
FIG. 5 shows a cross sectional view of a second embodiment of the present invention of FIG. 3 in an open position.

FIGS. 4 and 5 show an embodiment of the present device 61 in which there is no fluid passage formed in the plunger. Instead, the body contains a port 62 which provides the fluid connection to the downstream component 64, in this instance a piece of plastic piping. As shown in the closed position, the farthestmost end 66 of the first portion 68 of the plunger 70 seals off the downstream side of the device 61 from the upstream component 72. The port 62 is shown as being at a 90 degree angle to the length of the body, but it may be any other desired angle.

As shown in FIG. 5, when the device of FIG. 4 is opened, the farthestmost end 66 of the first portion 68 of the plunger 70 has been moved back from the face 72 providing a passageway 74 to the bore 76 and the port 62 so as to provide fluid communication between the upstream component 72 and the downstream component 64 through the device 61.

Figure 6:
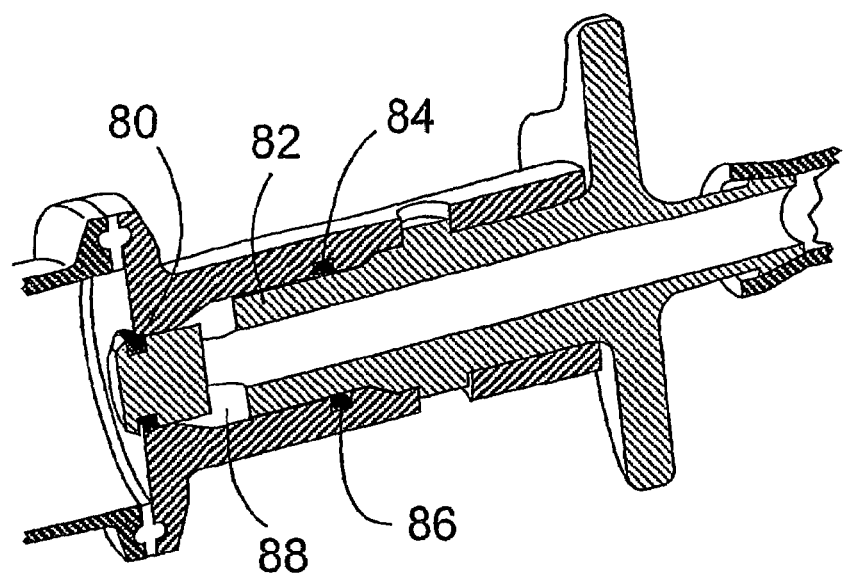
FIG. 6 shows a cross sectional view of another embodiment of the present invention.

As shown in FIGS. 1-5, the seals may be mounted on the plunger of the device. Further, the seals shown in FIGS. 1-5 are O-rings, either pre-formed and retained within grooves on the plunger or formed in place in the grooves of the plunger. However, if desired, different configurations of seals and their placements can be used. For example, FIG. 6 shows some seals 80 formed on the plunger 82 with other seals 84 held in grooves 86 in the inner surface of the bore 88.

Figure 7:
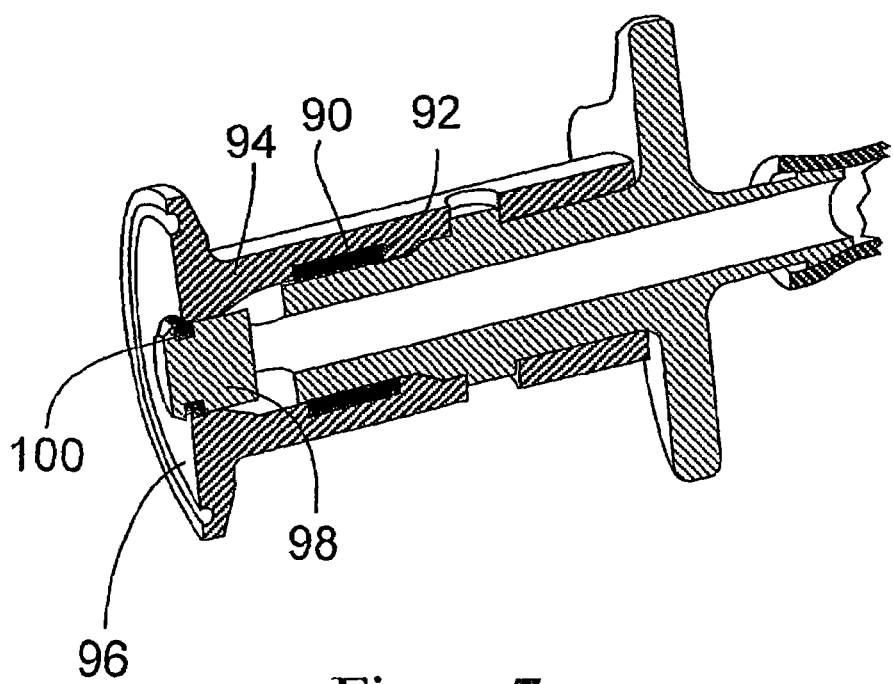
FIG. 7 shows a cross sectional view of another embodiment of the present invention.

FIG. 7 shows an embodiment with a linear or gland seal 90 is retained within a groove 92 on the inner wall of the body 94 and other seals 96 attached to the plunger 98 in grooves 100.

Figure 8:
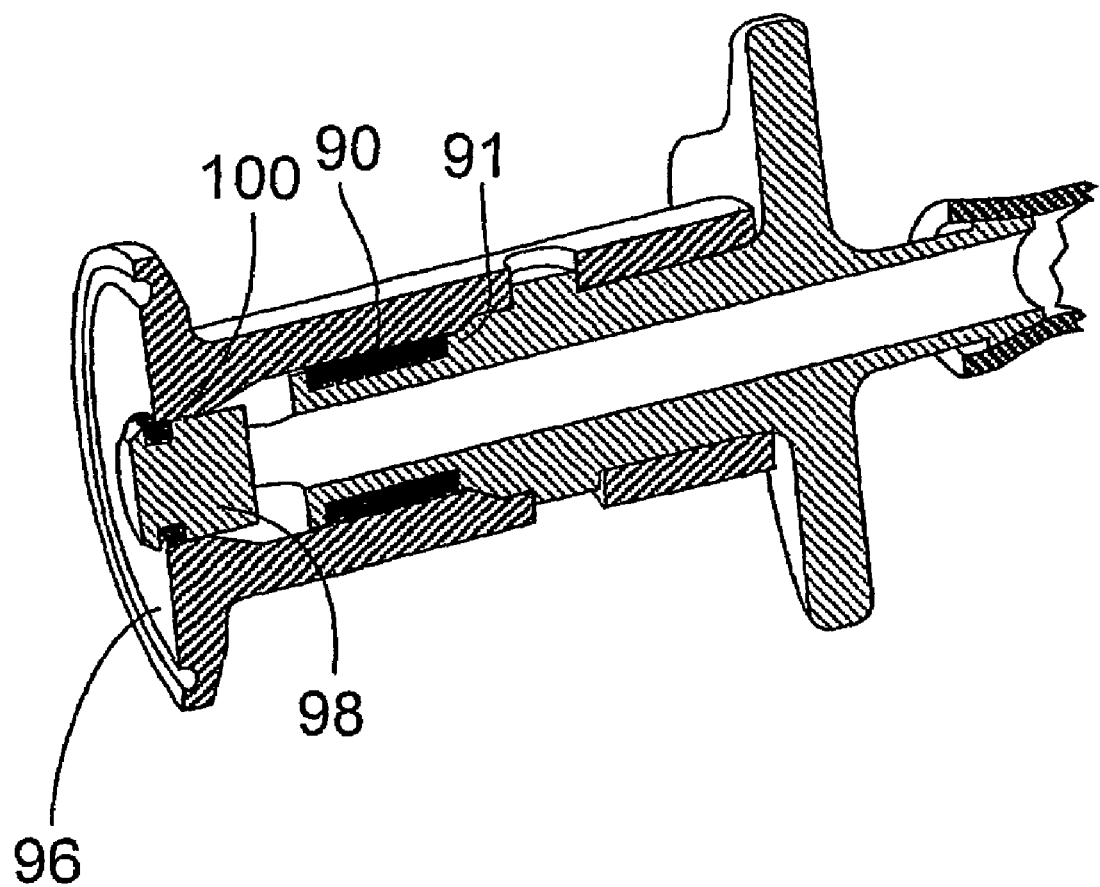
FIG. 8 shows a cross sectional view of another embodiment of the present invention.

FIG. 8 shows a similar design to that of FIG. 7 except that the gland seal 90 is formed on the outer wall 91 of the plunger 98 and other seals 96 are attached to the plunger 98 in grooves 100.

As this is device is provided in a sterile condition, i.e. the interior of the system and any component connected downstream of the device is pre-sterilized such as with gamma radiation, ethylene gas or the like and shipped in a sterile condition, some type of use indicator would be helpful so one knows when a system has been used and should therefore be replaced.

Figure 9A:
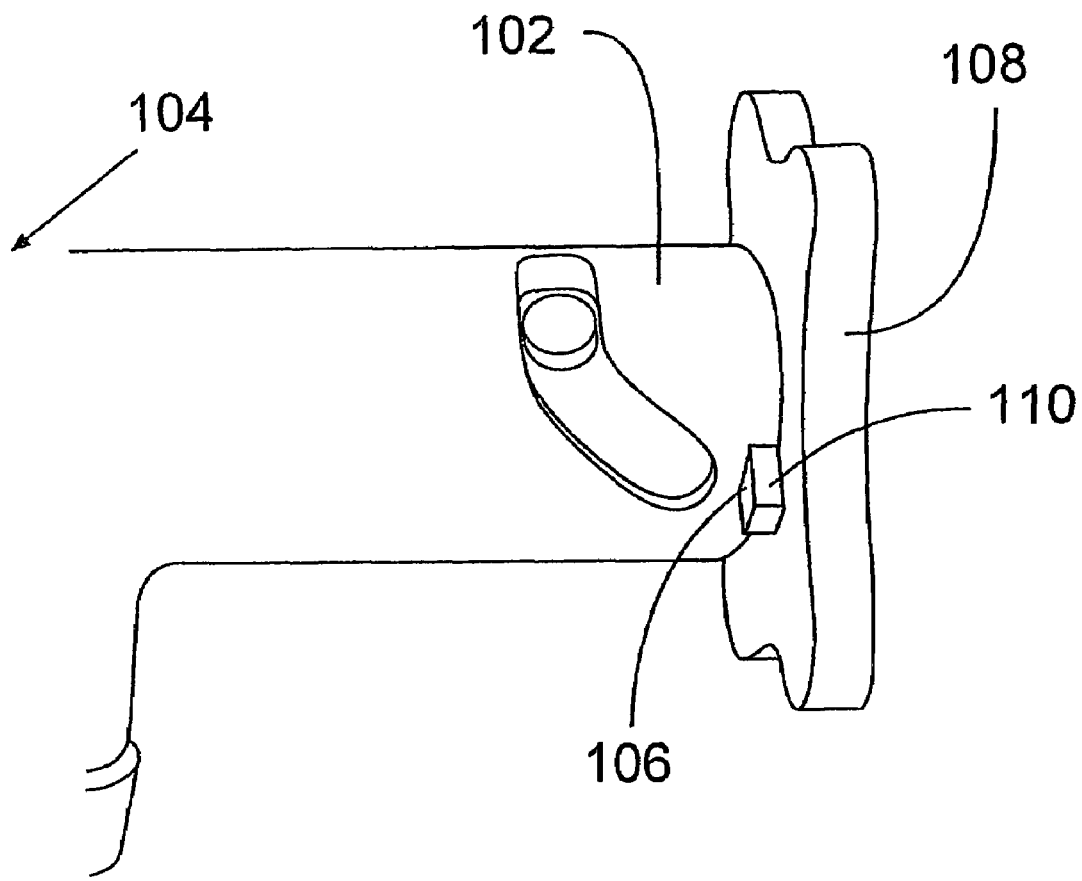
FIG. 9A shows a perspective view of a locking mechanism of the present invention in unopened condition.

FIG. 9A shows a first embodiment of an indicator useful on the present invention. As shown in the FIG. 9A, the body section 102 distal from the steamable face 104 has a series of one or indentations or locking recesses or fixed pawls 106. The plunger 108 has a mating detent 110 which is located in one of the recesses before the device is sterilized. The device is shipped in this sterile condition with the detent remaining in the recess. In fact, the detent/recess combination works to ensure that the device doesn't accidentally open due to vibration or handling during shipping.

Figure 9B:
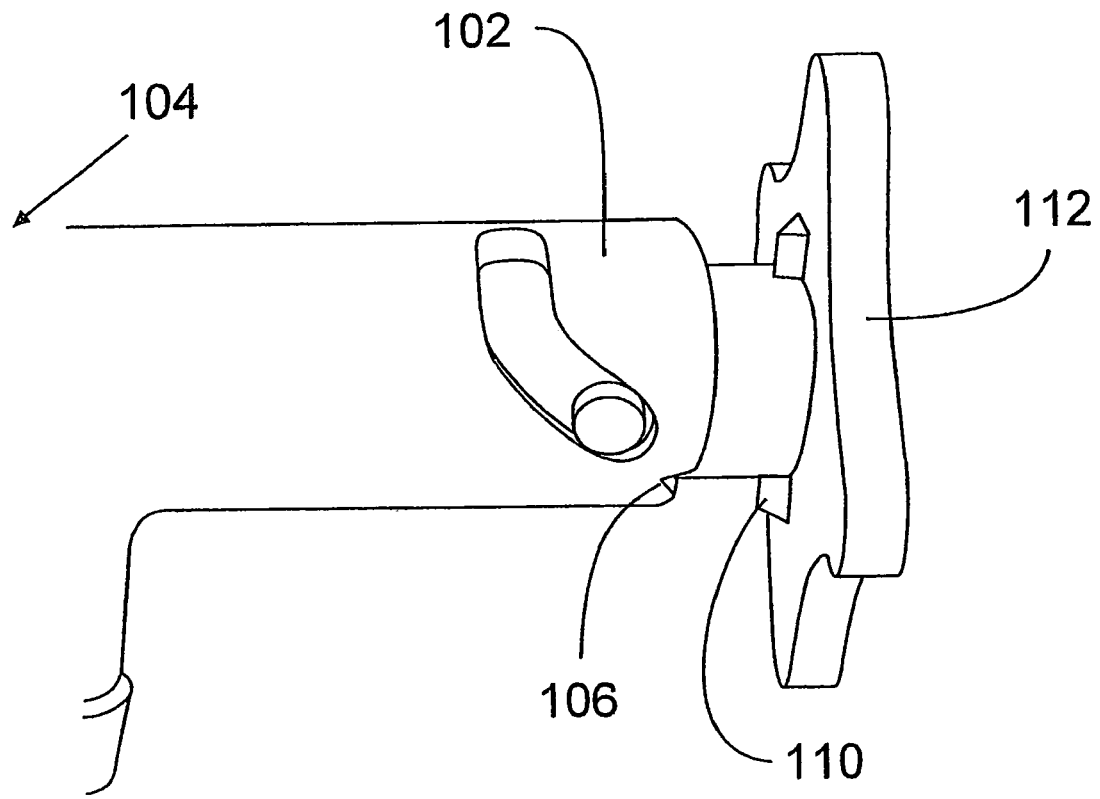
FIG. 9B shows a perspective view of the locking mechanism of 9A of the present invention in the opened condition.

The device is then taken from its sterile container in the closed position of 9A and attached by its face to the system. The face is then steam sterilized. The device is then opened by rotating the handle to an open position as shown in FIG. 9B.

Figure 9C:
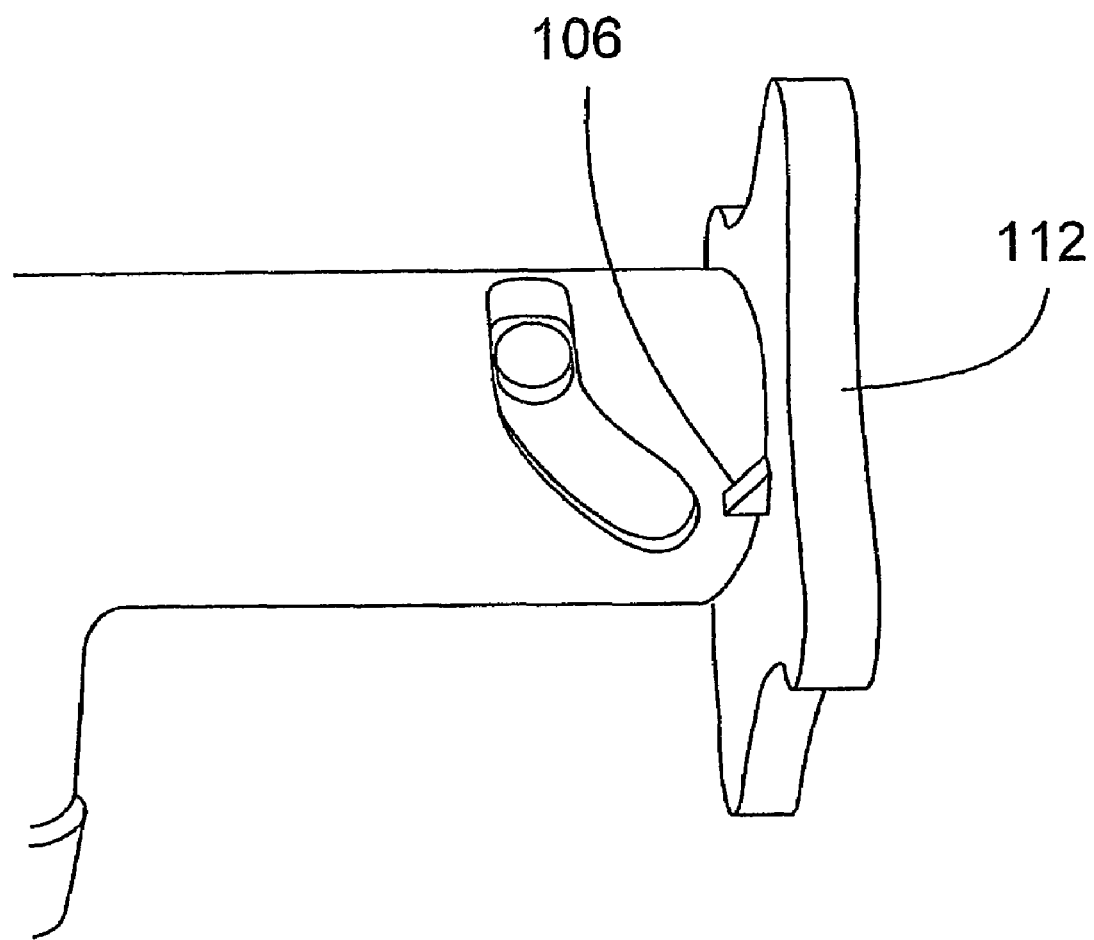
FIG. 9C shows a perspective view of the locking mechanism of 9A of the present invention in the reclosed position.

When the device is closed after use, the handle 112 of the plunger 108 is capable of moving the detent 110 past the first recess and into the second recess 106 as shown in FIG. 9C. This provides a visual indication to the user that the device is no longer sterile. In addition, it provides a manual indication to the user that the device has been used as the detent 110 has to be turned past the two recesses 106, each with an affirmative clicking action before the device can be opened. Moreover, one can design the walls of the farthermost (used condition) recess 106 so that the movement out of the recess requires an extraordinary amount of force to again indicate to the user that the device has been used and shouldn't be reused.

Figure 10A:
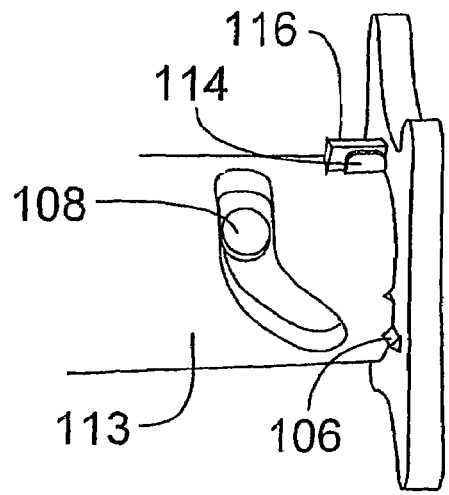
FIG. 10A shows a perspective view of a locking mechanism of the present invention in unopened condition.

FIG. 10A shows another embodiment of an indicator useful on the present invention. As shown in the FIG. 10A, the body section 113 distal from the steamable face (not shown) has a series of one or indentations or locking recesses or fixed pawls 106 as well as one or more breakaway tabs 114. The plunger 108 has a mating detent 110 which is located in one of the recesses 106 before the device is sterilized as well as a breaking bar 116. The device is shipped in this sterile condition with the detent remaining in the recess and the breaking bar being positioned behind the breakaway tab.

Figure 10B:
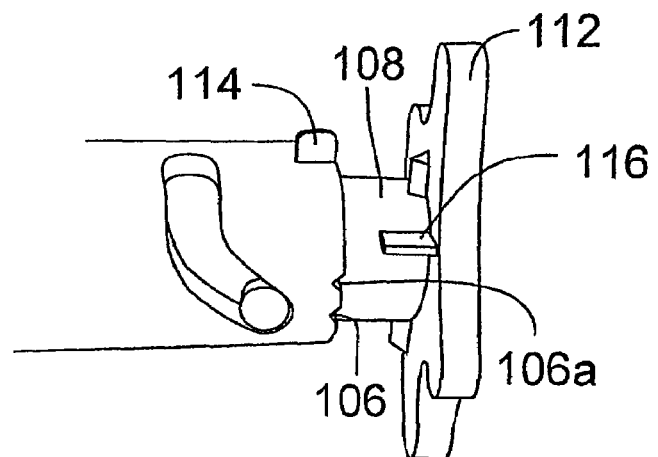
FIG. 10B shows a perspective view of the locking mechanism of 10A of the present invention in the opened condition.

The device is then taken from its sterile container in the closed position of 10A and attached by its face (not shown) to the system. The face is then steam sterilized. The device is then opened by rotating the handle 112 to an open position as shown in FIG. 10B. In doing so the breaking barn 16 rotates past and over the breakaway tab 114, causing it to be bent over or removed altogether.

Figure 10C:
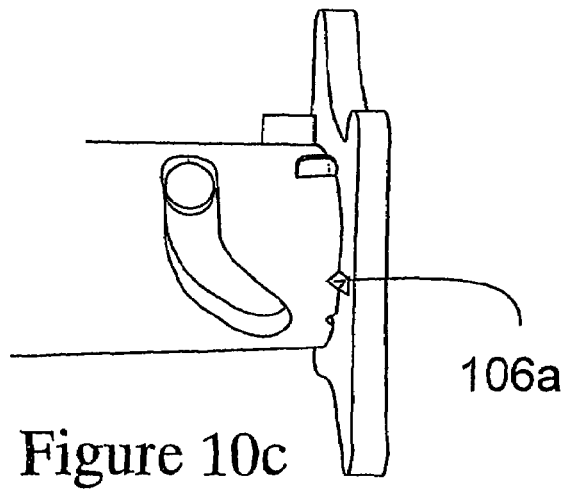
FIG. 10C shows a perspective view of the locking mechanism of 10A of the present invention in the reclosed position.

When the device is closed after use, the handle 112 is capable of moving the detent 110 past the first recess 106 and into the second recess 106A as shown in FIG. 10C.

Figure 11A:
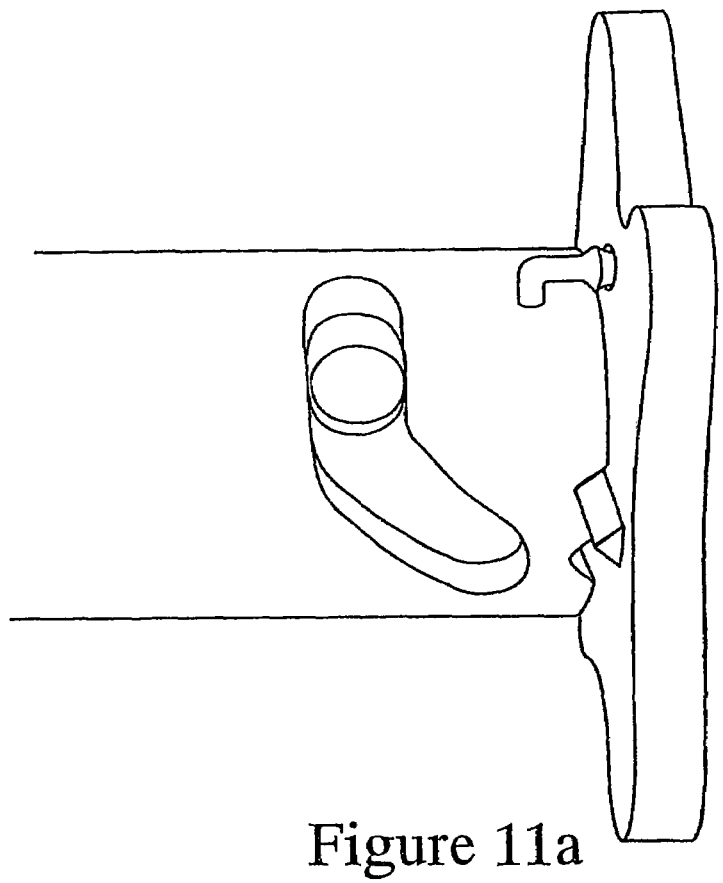
FIG. 11A shows a perspective view of a locking mechanism of the present invention in unopened condition.
Figure 11B:
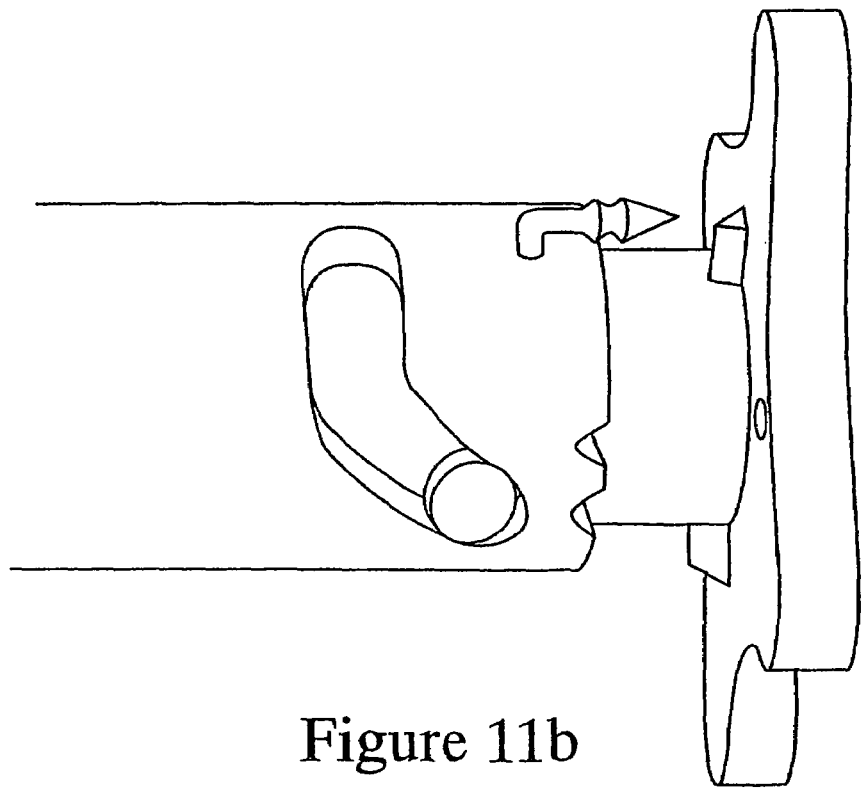
FIG. 11B shows a perspective view of the locking mechanism of 11A of the present invention in the opened condition.

FIGS. 11A and B show a plastic feature extending from the body that forms another breakaway (or bend-away) indicator. FIG. 11A, shows the valve in its shipped (or pre-sterilized) position. It is intended that when the valve is opened, this protruding feature will break away or at least bend away from its original position, thereby indicating that the valve has been actuated and should not be used again once it has been subsequently closed. FIG. 11B shows the valve in the open position, showing the tab feature as being bent.

Figure 12A:
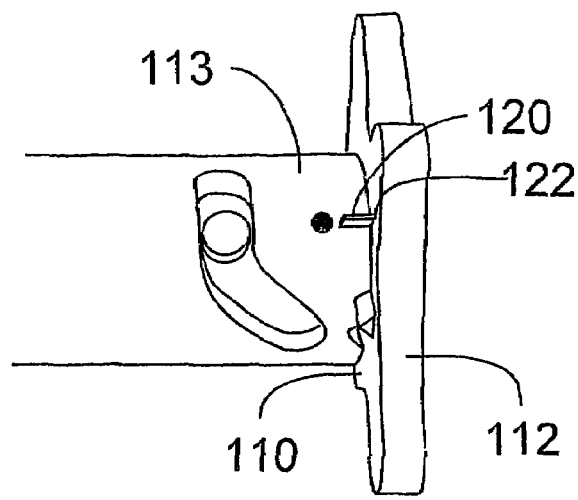
FIG. 12A shows a perspective view of a locking mechanism of the present invention in unopened condition.

FIG. 12A shows another embodiment of an indicator useful on the present invention. As shown in the FIG. 12A, the body section 113 distal from the steamable face (not shown) has a series of one or indentations or locking recesses or fixed pawls 106 as well as one or more tab retainers 120. The plunger 108 has a mating detent 110 which is located in one of the recesses 106 before the device is sterilized as well as a breakaway or fold over tab 122. The device is shipped in this sterile condition with the detent remaining in the recess and the breaking bar being positioned behind the breakaway tab.

Figure 12B:
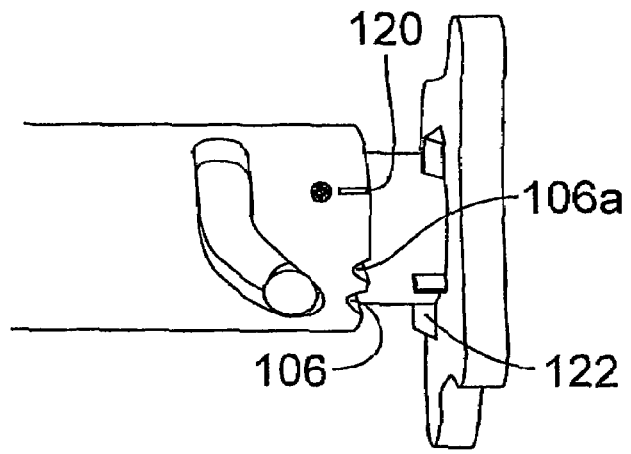
FIG. 12B shows a perspective view of the locking mechanism of 12A of the present invention in the opened condition.

The device is then taken from its sterile container in the closed position of 12A and attached by its face (not shown) to the system. The face is then steam sterilized. The device is then opened by rotating the handle 112 to an open position as shown in FIG. 12B. In doing so the tab 122 in tab retainer 120 rotates out of the retainer 120, causing it to be bent over or removed altogether.

Figure 12C:
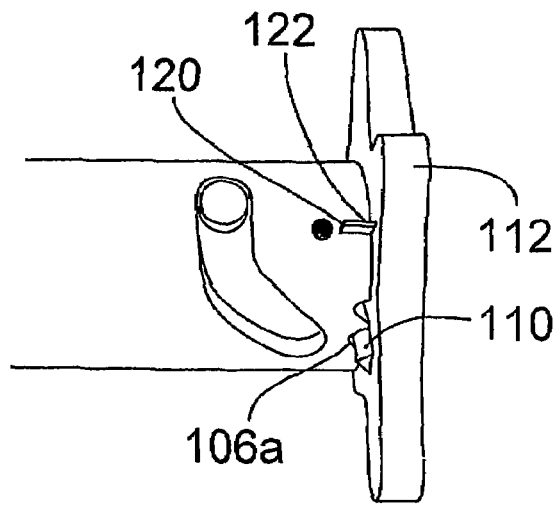
FIG. 12C shows a perspective view of the locking mechanism of 12A of the present invention in the reclosed position.

When the device is closed after use, the handle 112 is capable of moving the detent 110 past the first recess 106 and into the second recess 106A as shown in FIG. 12C with the tab 122 if it remains being bent up and not being returning to the retainer 120.

Figure 13:
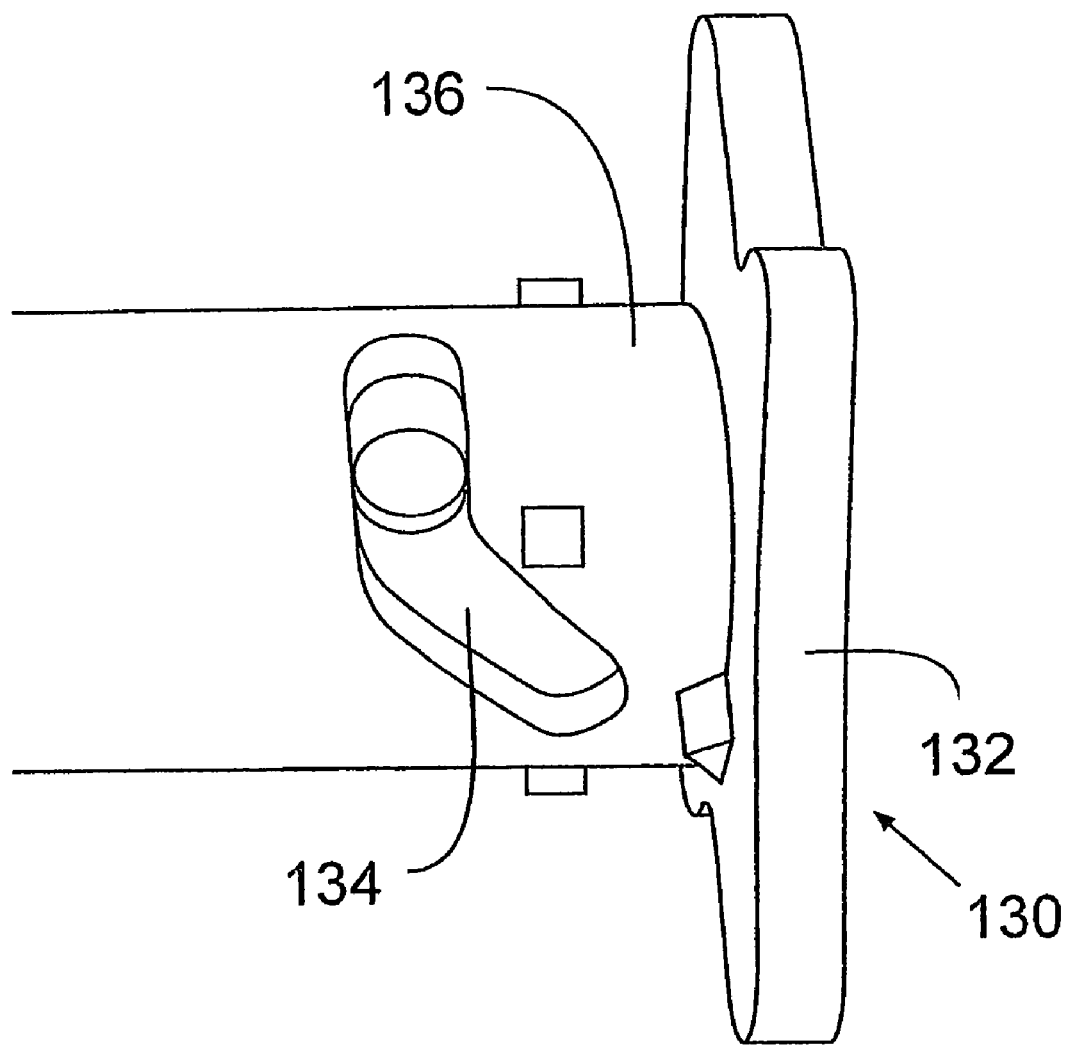
FIG. 13 shows a perspective view of a locking mechanism of the present invention in unopened condition.

As an alternative or in addition to any of the mechanisms discussed above, as shown in FIG. 13 one may use a shrink wrap indicator 130 over the device or at least the handle portion 132 of the plunger 134 and the surrounding body 136 of the device to indicate that the device is in an unopened condition.

Figure 14:
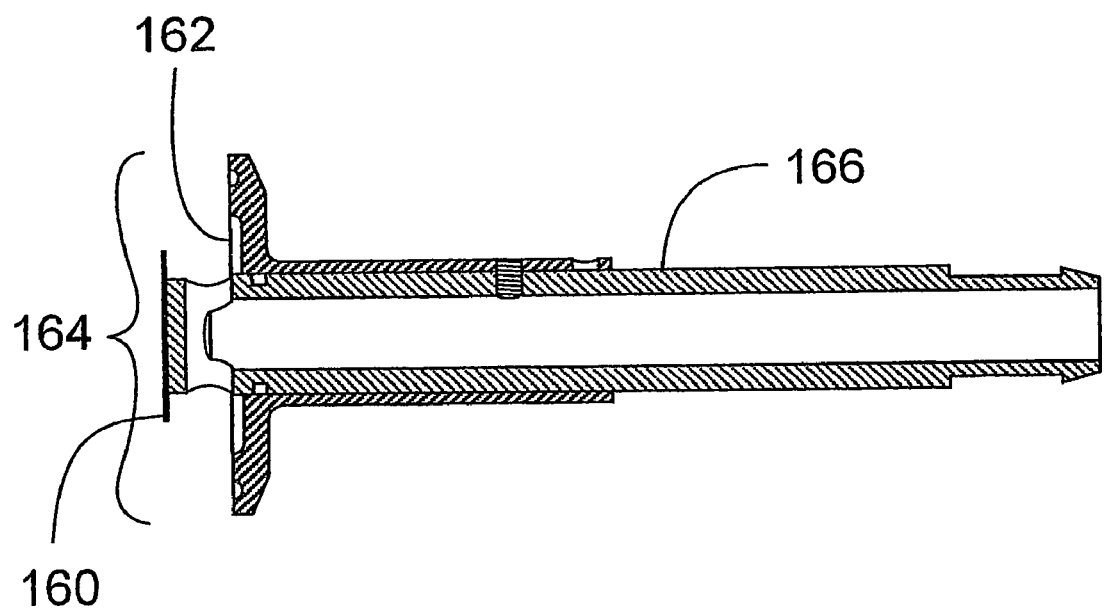
FIG. 14 shows an alternative design of the present invention.

As an alternative to the face of the device as shown in FIG. 1, one may use a foil 160, metal or plastic, such as PEI, PEEK, polysulphones, aluminum, stainless steel and the like, adhered to the body portion 162 of the face 164 and used to form the sterile seal as shown in FIG. 14. It is then pierced or penetrated by the plunger 166 to establish a fluid flow. A rubber septum in lieu of the foil could also be used. A scored surface can also be used. The foil may be adhered in a variety of manners that are well known in the art such as heat sealing, vibration welding such as ultrasonic welding, solvent bonding and through the use of adhesives such as epoxies and urethanes.

Figure 15:
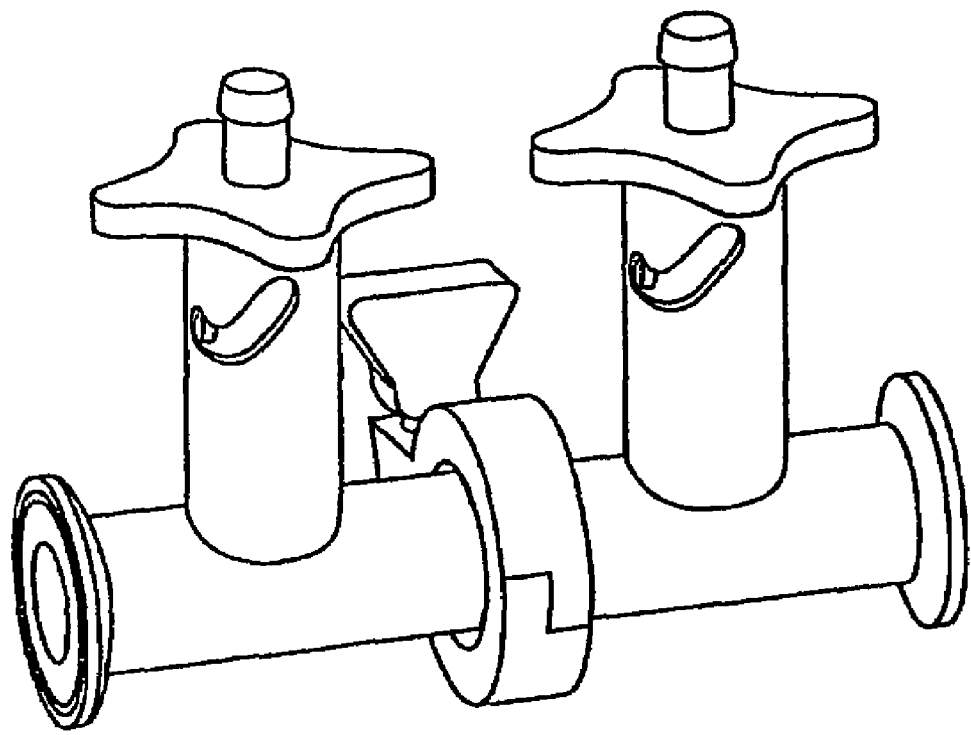
FIG. 15 shows another embodiment of the device of the present invention.

FIG. 15 shows another embodiment of the present invention. In this embodiment the body of the device is formed as an integral component of a pipe. Preferably the pipe is made of a steam resistant plastic (described below) or alternatively, it may be made of a metal such as stainless steel so long as it contains the necessary features of the present invention. The body can be formed as an arm of the piece as shown. The plunger (as shown being similar to that of FIG. 1) is then inserted into the body of the piece.

FIGS. 16 A-I show several other connectors devices that fall within the present invention. FIG. 16A is similar to the valve design of FIG. 14A. It is comprised of a body 180, and a plunger 181 contained within a bore 182 of the housing. The plunger has a fluid channel 185 connecting it in fluid communication to the rest of the downstream side of the device and beyond. A face 183 is formed by the outermost portion of the body 180 and plunger 181. Unlike the embodiment of FIG. 1, the bore 182 is essentially linear as is the plunger 181. As shown, the device is in its open position. The plunger 181 rather than retracting into the bore 12, is extended out from the bore to expose an opening or openings 184 so as to create fluid communication between one end and the other end of the device.

Figure 16A:
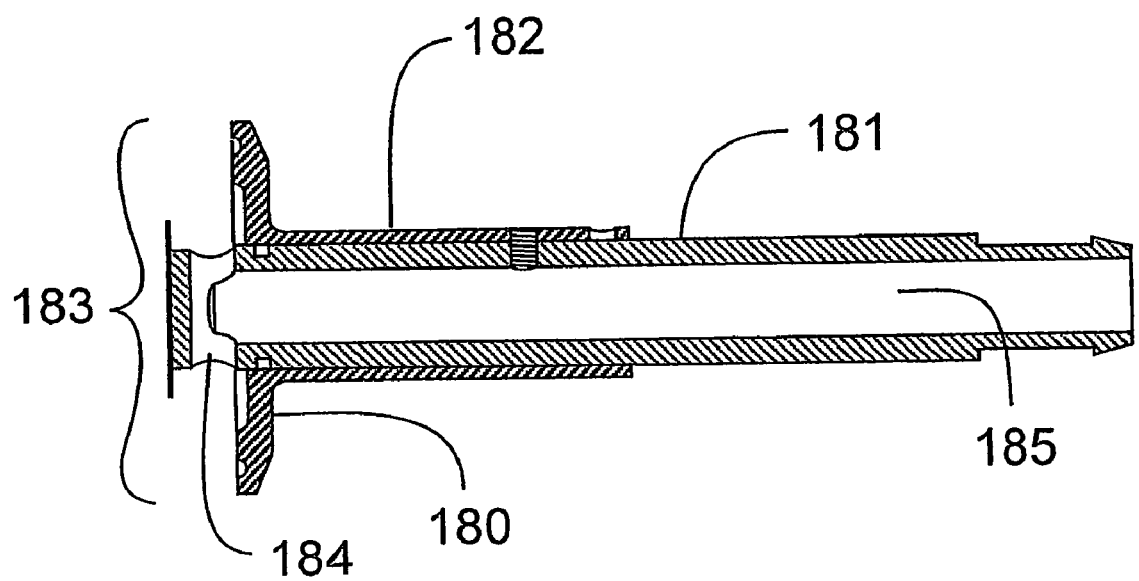
Figure 16B:
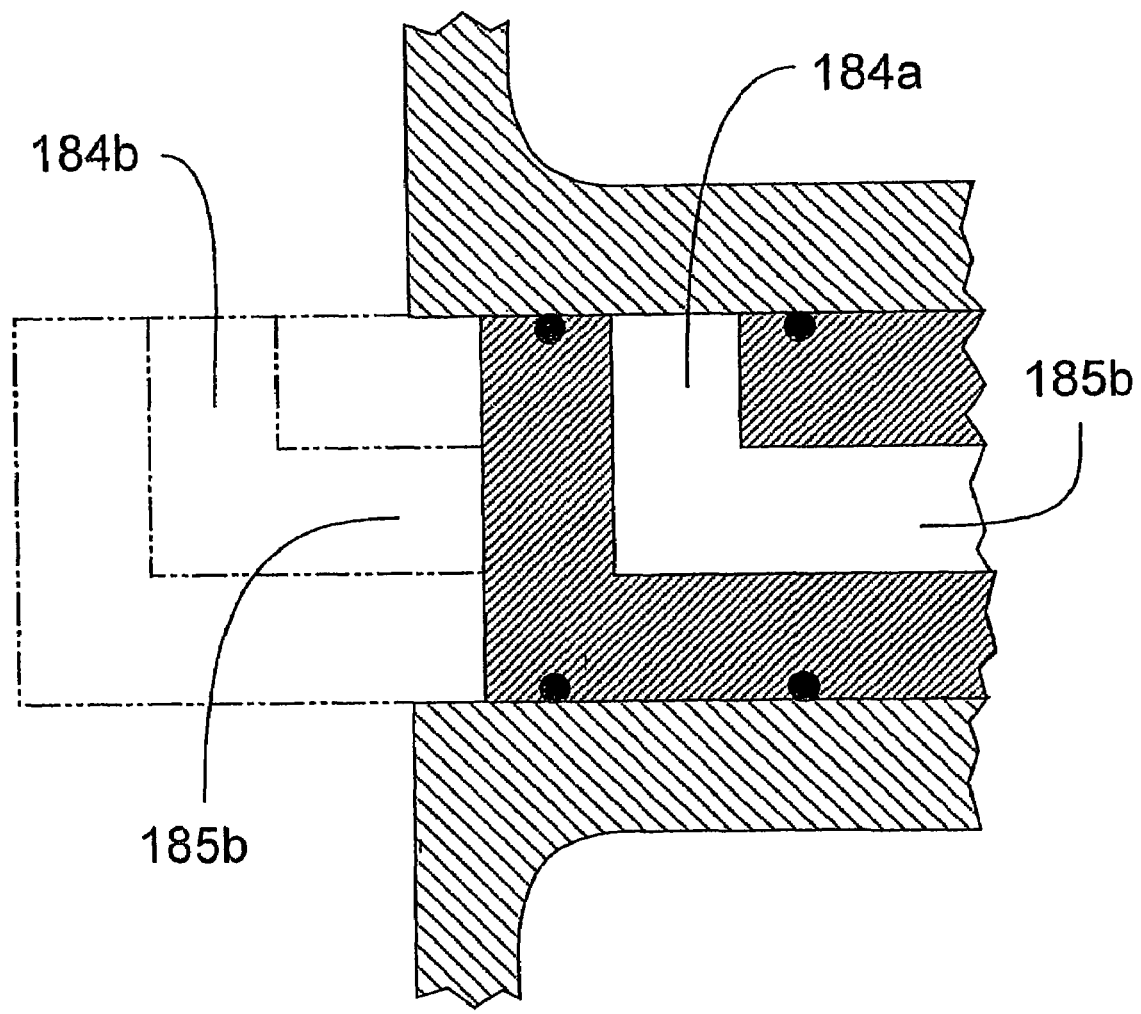

FIG. 16B shows a close up variant of the design of FIG. 16A. In this variant, the opening 184B is formed at a right angle to the fluid channel 185B only on one side of the plunger.

Figure 16C:
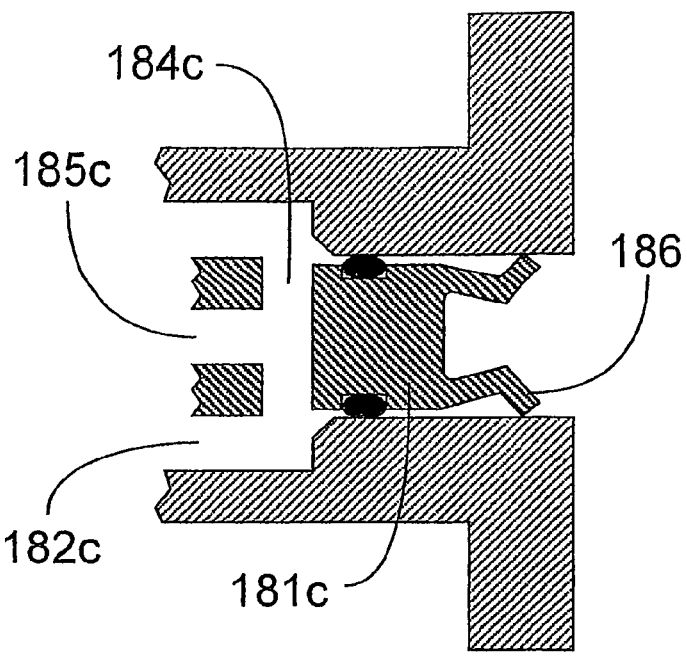
Figure 16D:
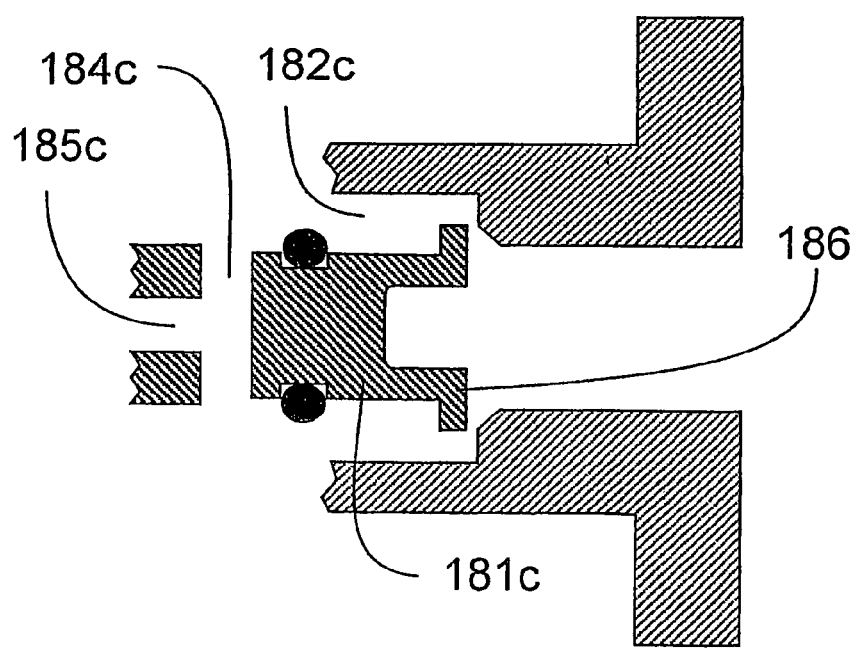

FIGS. 16C and D show a close up cross-sectional view of another embodiment. In this variant, the upstreammost portion of the plunger 181C is in the form of series of spring fingers 186. The plunger 181C is pulled back into the bore 182C to open the device as shown in FIG. 16D. Fluid then flows into the bore 182C, into openings 184C through the fluid channel 185C to the downstream component.

Figure 16E:
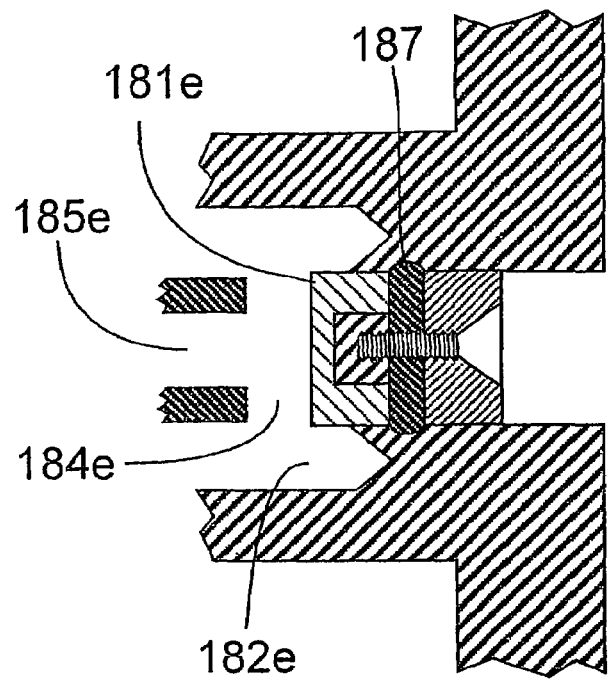
Figure 16F:
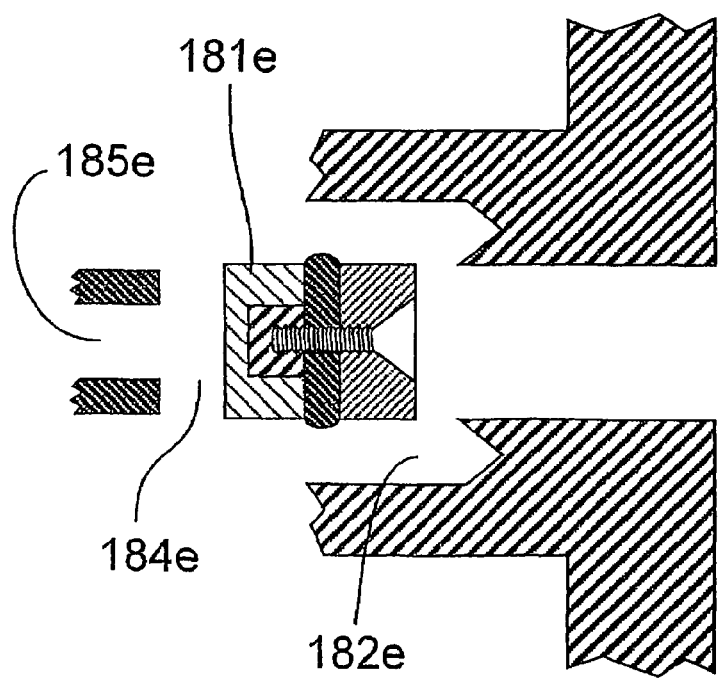

FIGS. 16E and F show a close up cross-sectional view of another embodiment. In this variant, the upstreammost portion of the plunger 181E is in the form of compression nut 187. The plunger 181E is pulled back into the bore 182E to open the device as shown in FIG. 16F. Fluid then flows into the bore 182E, into openings 184E through the fluid channel 185E to the downstream component.

Figure 16G:
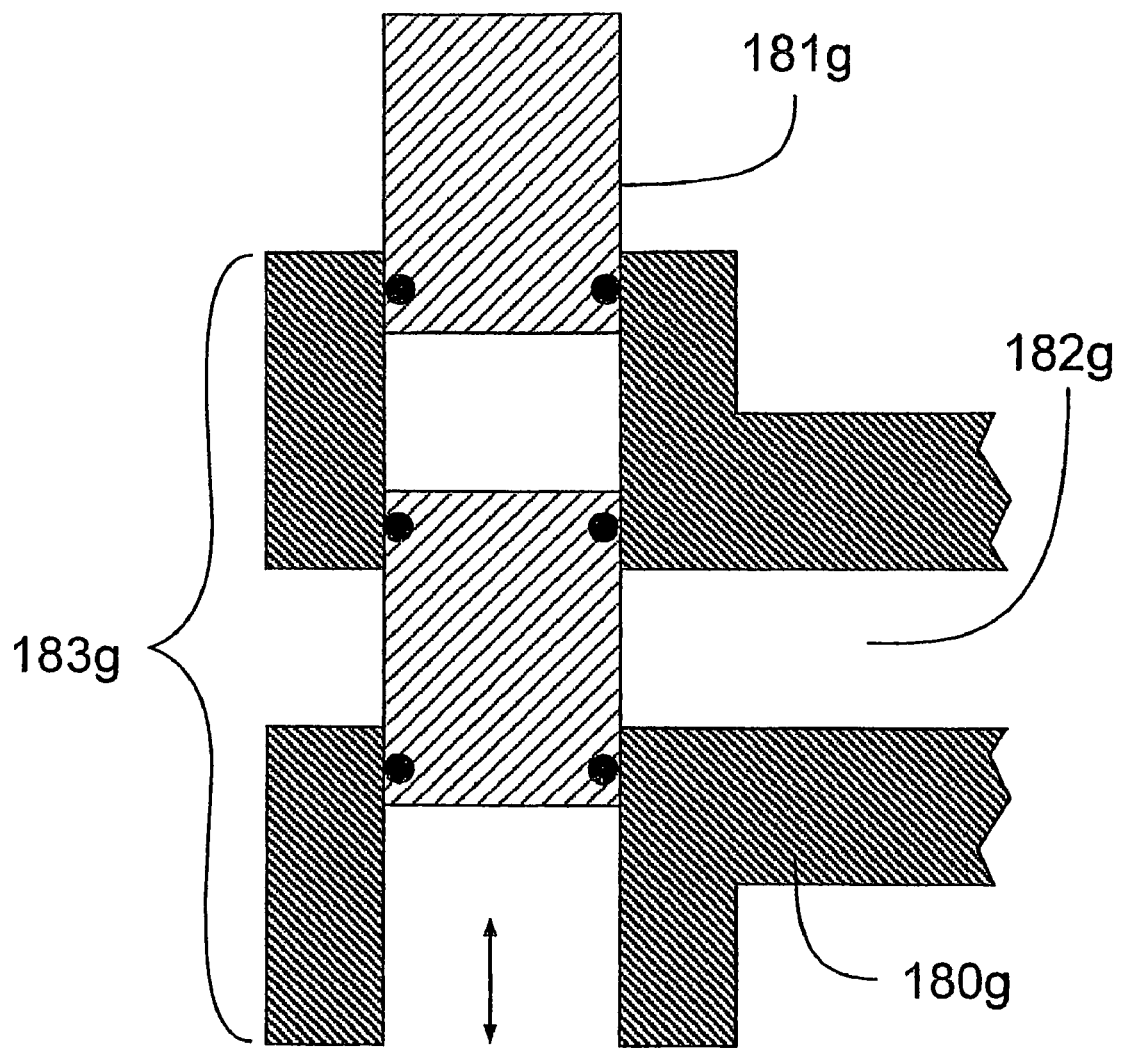

FIG. 16G shows another embodiment of the present invention. In this design, the plunger 181G is actually mounted to move laterally within the bore 182G of the housing 180G in a push/pull fashion to open and close the device. The face 183G is formed of the upstream end of the body and the plunger 181G as shown.

Figure 16H:
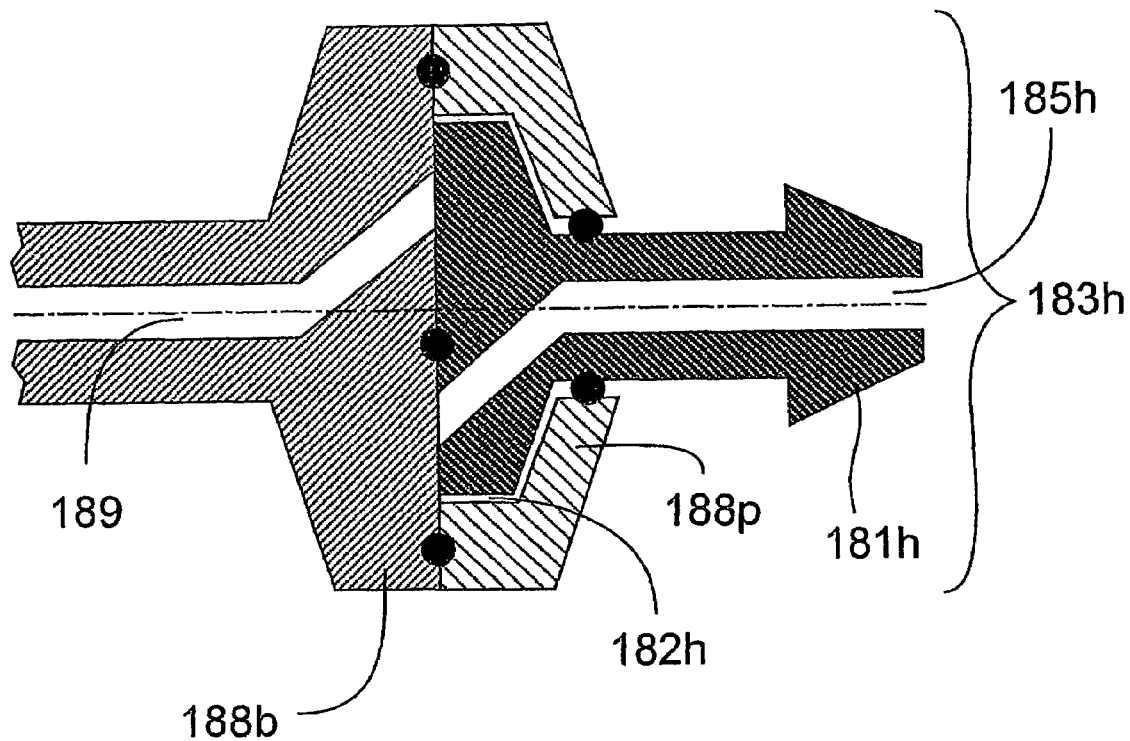

FIG. 16H shows a rotatable device with the body 180H being formed of two pieces 188A and 188B. The plunger 181H is contained within a portion of the bore 182H as shown. The plunger as shown is in the closed position. The face 183H is formed by the upstreammost portions of the plunger 182H and the body portion 188B. Also as shown the upstream component is attached to the plunger 181H. As the plunger is rotated from its closed to its open position, the fluid channel 185H of the plunger aligns with a fluid channel 189 of body portion 188B to establish fluid communication through the device.

Figure 16I:
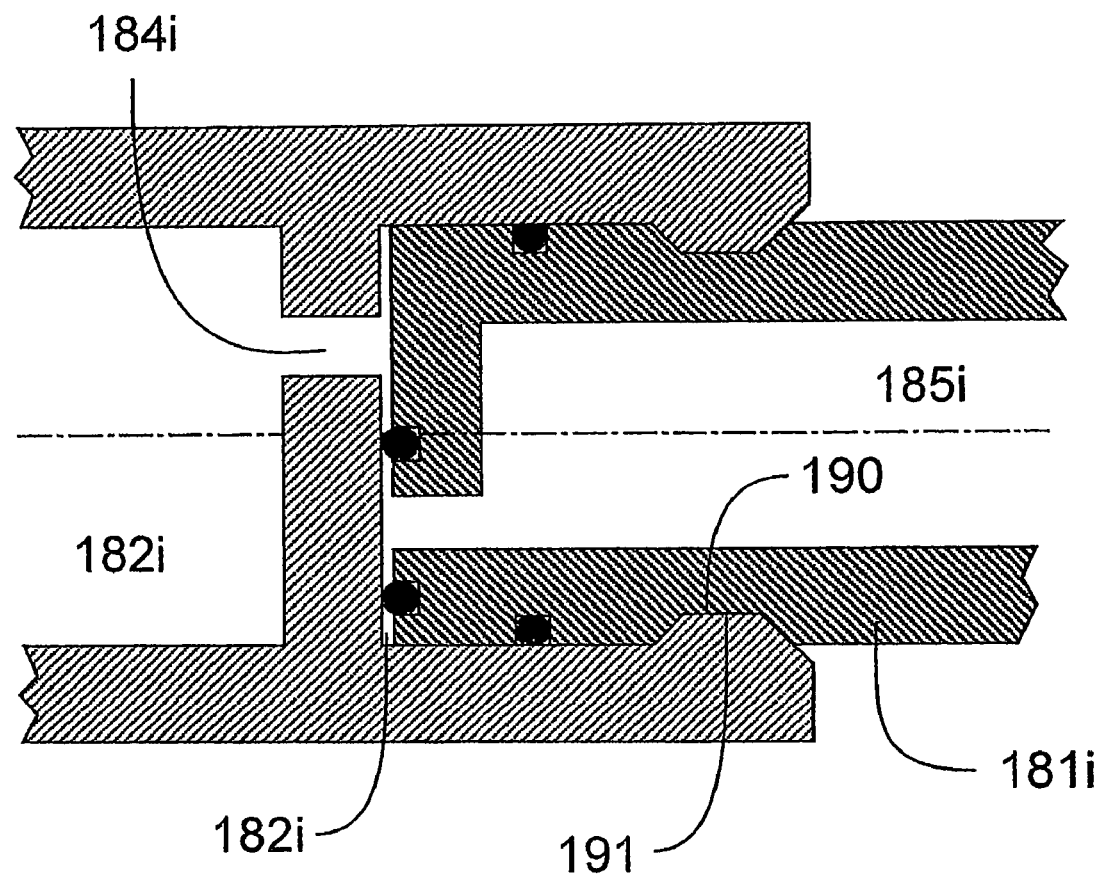

FIG. 16I shows another variant of the rotational design. Here the Plunger 181I is retained in the bore 182I of the body 180I by a groove 190 and abutment 191. When the plunger 181I is rotated to its open position, fluid may pass through the bore 182I into the fluid channel 185I through opening 184I.

FIG. 17 shows the device of the present invention in one potential application in which there is a sterile to nonsterile connection. As shown the fluid transfer device 200 of the embodiment shown in FIG. 3 is attached by its face (not shown) to a connection point 204 such as a "T" fitting on a process pipe 206 as shown. A clamp 202 holds the adjoining and mating faces (not shown, but see FIG. 3 for details of the mating assembly) of the device and the pipe 206 together in a liquid tight arrangement. The exit of the device 208 here in the form of a barb is connected to a tube 210 which in turn is connected to a collection bag 212. In use, the device 200 is in a closed position and has the tube 210 and bag 212 connected to it. The device with the tube and bag are then gamma sterilized (i.e. by gamma irradiation) or otherwise sterilized.

The device with the tube and bag is then attached to the pipe by the device face (not shown) by the clamp 202. The face is then steam sterilized along with the remainder of the system and is ready for use. When it is desired to fill the bag 212, one simply opens the device 200 by rotating the handle 214 which moves the plunger (not shown) away from the face creating an opening into the bore for the fluid to flow out the exit 208 through tube 210 and into the bag 212. Once the bag 212 is full, the handle is rotated the opposite direction to close the bore to the fluid. The bag 212 can then be closed off via a clamp or hemostat (not shown) and removed for further processing or use.

FIG. 18 shows a system using the device of the present invention wherein two sterile devices can be connected together. As shown, one can use a connector 300 formed of four interconnecting arms 302 A, B, C and D the end of each arm 302 A,B, C and D having a mating flange 304 A,B, C and D a first sterile transfer device 306 of the present invention in attached to arm 302A and a second device 308 is attached to a second arm 302B. A live steam line 310 is attached to arm 302C and a steam/condensate trap 312 is attached to arm 302D. Alternatively, one could attach a sterile barrier filter as taught by PCT/US01/47425, filed Dec. 3, 2001 and available from Millipore Corporation of Bedford, Mass. to arm 302D to remove the condensate after steaming.

Devices 306 and 308 are attached to other components of the system (not shown) and as with the embodiment of FIG. 14 are presterilized such as with gamma radiation before assembly the connector 300.

After assembly, steam enters through line 310 to sterilize the entire interior of connector 300 and the steamable faces of the devices 306 and 308. The steam then shut off and the steam/condensate is removed to the trap 312 which is then shut off from the connector 300. Devices 306 and 308 are then opened to form a sterile to sterile connection between them.

Other uses will be found for these devices. For example, they can be used to isolate a steam fragile component, such as some filters with steam sensitive membranes, in a process line. The filter especially in the form of a disposable capsule can be attached to the device and presterilized (such as by gamma). The device can then be connected to the line which is then steam sterilized and the device is then opened to provide fluid flow to the filter. If desired the inlet and outlet of the filter can contain such devices the outermost ends of which have the steam sterilizable face. Alternatively, a device can be attached to each end of a length of tube to form a sterile transfer pipe. Other uses can also be made of the present invention. Additionally, the connector of the present invention can be connected or actually molded into a disposable plastic container such as disposable process bag for the manufacture and transfer of biotech products. Such bags are readily available from companies such as Hyclone of Utah and Stedim of France.

The device is formed a plastic material and may be formed by machining the body and plunger assemblies and then applying the necessary seals and the like, or preferably by molding the body and the plunger separately and assembling them together with the necessary seals and other components.

The device may be made of any plastic material capable of withstanding in line steam sterilization. The temperature and pressure of such sterilization is typically about 121° C. and 1 bar above atmospheric pressure. In some instances, it may be desirable to use even harsher conditions such as 142° C. and up to 3 bar above atmospheric pressure. The body and at least the face of the plunger should be capable of withstanding these conditions. Preferably, the entire device is made of the same material and is capable of withstanding these conditions. Suitable materials for this device include but are not limited to PEI (polyetherimide), PEEK, PEK, polysulphones, polyarlysulphones, polyalkoxysulphones, polyethersulphones, polyphenyleneoxide, polyphenylenesulphide and blends thereof. Alternatively, one can make the face portion from ceramic or metal inserts alone or that are overmolded with a plastic cover One can also form a polymeric face with a metal outer layer using plasma coating processes.

The seals of the present invention can be made of a variety of materials typically used for making resilient seals. These materials include but are not limited to natural rubber, synthetic rubbers, such as silicone rubbers, including room temperature vulcanizable silicone rubbers, catalyzed (such as by platinum catalysts) silicone rubbers and the like, thermoplastic elastomers such as SANTOPRENE® elastomers, polyolefins such as polyethylene or polypropylene, especially those containing gas bubbles introduced either by a blowing agent or entrained gas such as carbon dioxide, PTFE resin, thermoplastic perfluoropolymer resins such as PFA and MFA resins available from Ausimont, USA of Thorofare, N.J. and E.I. DuPont de Nemours of Wilmington, Del., urethanes, especially closed cell foam urethanes, KYNAR® PVDF resin, VITON® elastomer, EPDM rubber, KALREZ resin and blends of the above.

Suitable materials for molded in place seals can be curable rubbers, such as room temperature vulcanizable silicone rubbers, thermoplastic elastomers such as SANTOPRENE® elastomers, polyolefins such as polyethylene or polypropylene, especially those containing gas bubbles introduced either by a blowing agent or entrained gas such as carbon dioxide and elastomeric fluoropolymers Other materials used in the devices should also be FDA grade components such as FDA grade silicones, PTFE resins and the like.

The present invention provides a sterile and steam sterilizable connecting device for fluid transfer. It may be single actuation (one open one close) or it may be multiple actuations with a single sterile connection (multiple openings and closings so long as the sterile connection upstream and downstream is maintained). Additionally, with the use of multiple seals or seals of long length, one is able to ensure that the sterility of the device is maintained even with multiple actuations.

What is claimed:

1. A sterile transfer device for fluids comprised of a body having a bore formed through at least a portion of its interior, a movable plunger contained within the bore, wherein the body and the plunger are formed of plastic, the body having a first and a second end, the first end containing a face designed to be attached to an upstream component, the plunger having a corresponding first and second end, the plunger having a shape corresponding to that of the bore and being of a diameter less than that of the bore, a port formed on the component selected from the group consisting of the second end of the plunger and a portion of the body downstream of the first end of the body, the port being connected to a downstream component, one or more seals between the plunger and the bore to form a liquid tight seal between various portions of the plunger and the bore, the first end of the plunger when in a closed position being in alignment with the face of the body, which combined, form a steamable surface and a sterile barrier against the environment to the rest of the interior of the body, the plunger and downstream components and a cam slot formed in the body, a cam formed on an outer surface of the plunger and contained within the cam slot and a handle formed on the plunger to move the plunger within the bore from a closed to an open and then back to a closed position, wherein the cam remains within the cam slot as the plunger moves from a closed position to an open and back to a closed position.

2. The device of claim 1 wherein the bore is a central bore formed through the entire length of the body.

3. The device of claim 1 wherein the device is formed of a plastic selected from the group consisting of polyetherimides (PEI), polyetheretherketone(PEEK), polyetherketone(PEK), polysulphones, polyarylsulphones, polyalkoxysulphones, polyethersulphones, polyphenyleneoxide, polyphenylenesulphide and blends thereof.

4. The device of claim 1 wherein the device is formed of polyetherimides(PEI).

5. The device of claim 1 wherein the first face of the body is in the form of a sanitary flange.

6. The device of claim 1 wherein the one or more seals are arranged along the outer surface of the plunger to form a liquid tight seal between various portions of the plunger and the bore.

7. A sterile transfer device for fluids comprised of a body having a bore formed through at least a portion of its interior, a movable plunger contained within the bore, the body having a first and a second end, the first end containing a face designed to be attached to an upstream component, the plunger having a corresponding first and second end, the plunger having a shape corresponding to that of the bore and being of a diameter less than that of the bore, a port formed on the component selected from the group consisting of the second end of the plunger and a portion of the body downstream of the first end of the body, the port being connected to a downstream component, the first end of the plunger when in a closed position being in alignment with the face of the body, which combined, form a steamable surface and a sterile barrier against the environment to the rest of the interior of the body, the plunger and downstream components and a cam slot formed in the body, a cam formed on an outer surface of the plunger and contained within the cam slot and a handle formed on the plunger to move the plunger within the bore from a closed to an open and then back to a closed position, wherein at least the first face of the body and the plunger are formed of a material selected from the group consisting of polyetherimides(PEI), polyetheretherketone(PEEK), polyetherketone(PEK), polysulphones, polyarylsulphones, polyalkoxysulphones, polyethersulphones, polyphenyleneoxide, polyphenylenesulphide and blends thereof.

8. The device of claim 7 wherein the first face of the body is in the form of a sanitary flange.

9. A sterile transfer device for fluids comprised of a body having a bore formed through at least a portion of its interior, the bore having three sections each with a different diameter, the body having a first and a second end, the first end containing a face designed to be attached to an upstream component, a movable plunger contained within the bore, the plunger having a shape corresponding to that of the bore and being of a diameter less than that of the bore, the plunger having a corresponding first and second end, the second end of the plunger being connected to a downstream component, the first end of the plunger when in a closed position being in alignment with the face of the body, which combined, form a steamable surface and a sterile barrier against the environment to the rest of the interior of the body, one or more seals between the plunger and the bore to form a liquid tight seal between various portions of the plunger and the bore, and a cam slot formed in the body, a cam formed on an outer surface of the plunger and contained within the cam slot and a handle formed on the plunger to move the plunger within the bore of the body, wherein the cam remains within the cam slot as the plunger moves from a closed position to an open and back to a closed position.

10. The device of claim 9 wherein the bore has a first bore section of a first set diameter, a second bore section of a second set diameter greater than the first set diameter and a transition section between the first and second sections having a tapering diameter along its length from the first section to the second section which is a progression of the difference in diameters between the first set diameter and the second set diameter.

11. The device of claim 9 wherein the bore has a first bore section of a first set diameter, a second bore section of a second set diameter greater than the first set diameter and a transition section between the first and second sections having a tapering diameter along its length from the first section to the second section which is a progression of the difference in diameters between the first set diameter and the second set diameter and the progression is linear.

12. The device of claim 9 wherein the plunger has one or more openings adjacent the first end and a fluid channel connecting the one or more openings to the second end of the plunger.

13. A sterile transfer device for fluids comprised of a body having a bore formed through at least a portion of its interior, a movable plunger contained within the bore, wherein the body and the plunger are formed of plastic, the body having a first and a second end, the first end containing a face designed to be attached to an upstream component wherein the first face of the body is in the form of a sanitary flange, the plunger having a corresponding first and second end, the plunger having a shape corresponding to that of the bore and being of a diameter less than that of the bore, a port formed on the component selected from the group consisting of the second end of the plunger and a portion of the body downstream of the first end of the body, the port being connected to a downstream component, the first end of the plunger when in a closed position being in alignment with the face of the body, which combined, form a steamable surface and a sterile barrier against the environment to the rest of the interior of the body, the plunger and downstream components, one or more seals between the plunger and the bore to form a liquid tight seal between various portions of the plunger and the bore, and a cam slot formed in the body, a cam formed on an outer surface of the plunger and contained within the cam slot and a handle formed on the plunger to move the plunger within the bore from a closed to an open and back to a closed position.

14. A sterile transfer device for fluids comprised of a body having a bore formed through at least a portion of its interior, a movable plunger contained within the bore, wherein the body and the plunger are formed of plastic, the body having a first and a second end, the first end containing a face designed to be attached to an upstream component wherein the first face of the body is in the form of a sanitary flange, the plunger having a corresponding first and second end, one or more seals between the plunger and the bore to form a liquid tight seal between various portions of the plunger and the bore, a port formed on the component selected from the group consisting of the second end of the plunger and a portion of the body downstream of the first end of the body, the port being connected to a tube which in turn is connected to a collection bag, the first end of the plunger when in a closed position being in alignment with the face of the body, which combined, form a steamable surface and a sterile barrier against the environment to the rest of the interior of the body, the plunger and downstream components and a cam slot formed in the body, a cam formed on an outer surface of the plunger and contained within the cam slot and a handle formed on the plunger to move the plunger within the bore from a closed to an open and back to a closed position.

15. The device of claim 14 wherein the port has a barb for attaching the tube to the port.

16. The device of claim 14 wherein the plunger has a shape corresponding to that of the bore and being of a diameter less than that of the bore.

17. A device comprising a valve having a face and a body, wherein the face is adapted to attach to an upstream component and includes at least one opening, the body having a bore extending at least part way through the body, a plunger contained at least partially in the bore and fitting within the opening of the face, the plunger having a first portion and a second portion, a port formed on the component selected from the group consisting of the second end of the plunger and a portion of the body downstream of the first end of the body, one or more seals disposed on the plunger between the first portion and the second portion wherein the one or more seals are adapted to sealingly mate with the bore of the body to seal from the environment the bore, wherein the plunger is movable between an open and a closed position, the one or more seals of the plunger engage with and seals the opening of the face when the plunger is within the opening in a closed position and a cam formed on the plunger and a cam slot formed in the body to limit the length of travel of the plunger in the bore when the plunger is moved to its open position by the handle, wherein the cam remains within the cam slot as the plunger moves from a closed position to an open and back to a closed position.

18. A device for fluid sampling comprising a valve having a face and a body, wherein the face is adapted to attach to an upstream component and includes at least one opening, the body having a bore extending at least part way through the body, a plunger contained at least partially in the bore and fitting within the opening of the face, the plunger having a first portion and a second portion, a port formed on the device selected from the group consisting of the second end of the plunger and a portion of the body downstream of the first end of the body, the port being connected to a tube which in turn is connected to a collection bag, one or more seals disposed on the plunger between the first portion and the second portion wherein the one or more seals are adapted to sealingly mate with the bore of the body to seal from the environment the bore, wherein the plunger is movable between an open and a closed position by a handle that moves the plunger linearly within the bore, the one or more seals of the plunger engage with and seals the opening of the face when the plunger is within the opening in a closed position and a cam formed on the plunger and a cam slot formed in the body to limit the length of travel of the plunger in the bore when the plunger is moved to its open position by the handle.

19. A sterile transfer device for fluids, comprising:
   a body having a bore formed through at least one portion of its interior, the body having a first end and a second end, the first end having a face designed to be connectable to an upstream component;
   a movable plunger contained within the bore, the plunger having a first end and a second end corresponding to the first end and the second end of the body, the plunger having a shape corresponding to that of the bore and being of a diameter less than that of the bore, the first end of the plunger when in a closed position being in alignment with the face of the body and forming a steamable surface and a sterile barrier against the environment to the rest of the interior of the body;
   a port connectable to a downstream component; and
   one or more seals between the plunger and the bore to form a liquid tight seal between various portions of the plunger and the bore.

20. The device of claim 19, further comprising a handle formed on the plunger to move the plunger within the bore from a closed to an open and then back to a closed position.

21. the device of claim 19, further comprising a cam slot formed in the body, a cam formed on an outer surface of the plunger and contained within the cam slot, wherein the cam remains within the cam slot as the plunger moves from a closed position to an open and back to a closed position.

22. The device of claim 19, further comprising a cam slot formed in the body, a cam formed on an outer surface of the plunger and contained within the cam slot and a handle formed on the plunger to move the plunger within the bore from a closed to an open and then back to a closed position, wherein the cam remains within the cam slot as the plunger moves from a closed position to an open and back to a closed position.

23. The device of claim 19, wherein the one or more seals form a liquid tight seal between various portions of the plunger and the bore when they are in the open position.

* * * * *

UNITED STATES PATENT AND TRADEMARK OFFICE
CERTIFICATE OF CORRECTION

PATENT NO. : 7,927,316 B2  
APPLICATION NO. : 10/500077  
DATED : April 19, 2011  
INVENTOR(S) : Stephen Proulx et al.

Page 1 of 1

It is certified that error appears in the above-identified patent and that said Letters Patent is hereby corrected as shown below:

Please add on the front page of the patent, immediately following
  "Prior Publication Data
US 2005/0016620 A1 Jan. 27, 2005":

-- Related U.S. Application Data
Provisional application No. 60/375,747, filed on April 26, 2002 --

Signed and Sealed this
Twenty-seventh Day of November, 2012

David J. Kappos
*Director of the United States Patent and Trademark Office*